United States Patent [19]

Moore, Jr.

[11] Patent Number: 5,961,968
[45] Date of Patent: *Oct. 5, 1999

[54] USE OF ALUM TO INHIBIT AMMONIA VOLATILIZATION AND TO DECREASE PHOSPHOROUS SOLUBILITY IN POULTRY LITTER

[75] Inventor: Philip A. Moore, Jr., Fayetteville, Ak.

[73] Assignees: Trustees of University of Arkansas, Fayetteville, Ak.; The United States of America as represented by the Secretary of Agriculture, Washington, D.C.

[*] Notice: This patent is subject to a terminal disclaimer.

[21] Appl. No.: 08/640,623

[22] Filed: May 1, 1996

Related U.S. Application Data

[62] Division of application No. 08/437,991, May 10, 1995, Pat. No. 5,622,697, and a division of application No. 08/129,742, Sep. 30, 1993, abandoned.

[51] Int. Cl.$^6$ ........................................................ A61L 9/01
[52] U.S. Cl. ............................ 424/76.6; 119/171; 422/4; 422/5; 424/682; 424/698
[58] Field of Search .................................. 424/76.6, 682, 424/698; 119/171; 422/4, 5

[56] References Cited

U.S. PATENT DOCUMENTS

| | | | |
|---|---|---|---|
| 3,029,783 | 4/1962 | Sawyer, Jr. et al. ..................... | 119/173 |
| 4,028,238 | 6/1977 | Allan . | |
| 4,034,078 | 7/1977 | Van Horn ............................... | 424/76.6 |
| 4,209,335 | 6/1980 | Katayama et al. . | |
| 4,306,516 | 12/1981 | Currey ...................................... | 119/113 |
| 5,039,481 | 8/1991 | Pacifici et al. .......................... | 424/76.6 |
| 5,176,879 | 1/1993 | White et al. ............................ | 424/76.6 |
| 5,362,842 | 11/1994 | Graves et al. ........................... | 528/262 |
| 5,589,164 | 12/1996 | Cox et al. ............................... | 424/76.5 |
| 5,609,123 | 3/1997 | Luke et al. .............................. | 119/173 |
| 5,634,431 | 6/1997 | Reddy et al. ........................... | 119/173 |

FOREIGN PATENT DOCUMENTS

| | | |
|---|---|---|
| 0 156 924 B1 | 10/1985 | European Pat. Off. . |
| 0 557 078 A1 | 8/1993 | European Pat. Off. . |
| 7-163641 | 6/1995 | Japan . |
| 84/02334 | 6/1984 | WIPO . |

OTHER PUBLICATIONS

Derwent Assession No. 1990–122131.
Chemical Abstracts 104:173975, "Manure Deodorizing Agent", Dec. 1985.
Chemical Abstracts 112:204041, "Deodorant Composition for Air", Jun. 1989.

*Primary Examiner*—Robert H. Harrison
*Attorney, Agent, or Firm*—Needle & Rosenberg, P.C.; Arthur J. Plantamura

[57] ABSTRACT

A method for treating poultry litter which inhibits ammonia volatilization and reduces soluble phophorus levels in the litter. The method comprises the addition of alum to litter in an amount sufficient to maintain the litter pH at values low enough to inhibit ammonia volatilization. The addition of alum, iron or calcium compounds to litter also effectively precipitates soluble phosphorus in litter, thereby reducing the amount of soluble phosphorus runoff from fields receiving litter.

9 Claims, 9 Drawing Sheets

USE OF ALUM TO INHIBIT AMMONIA VOLATILIZATION AND TO DECREASE PHOSPHOROUS SOLUBILITY IN POULTRY LITTER

This is a division of application Ser. No. 08/437,991, filed May 10, 1995, now U.S. Pat. No. 5,622,697 and a division of application Ser. No. 08/129,742, filed Sep. 30, 1993, abandoned.

BACKGROUND OF THE INVENTION

The present invention relates to a method for inhibiting ammonia volatilization in poultry litter. The present invention further relates to a method for reducing phosphorus solubility in poultry litter.

One of the major problems encountered in raising chickens, turkeys or laying hens under confined conditions is ammonia volatilization, the production of excessive levels of ammonia gas ($NH_3$). As volatilization occurs, ammonia levels can reach as high as 100–200 ppm in poultry houses. For over 30 years, researchers have shown that excessive ammonia buildup in poultry rearing facilities adversely affects both poultry and farm workers. Scarborough (*Delaware Agric. Exp. Stn. Prog. Rep.*, NE8, 1957) and Valentine (*Br. Poultry Sci.* 5:149–159, 1964) both observed ammonia levels in the 60 to 70 ppm range in the atmosphere of poultry houses. Ammonia levels reaching as high as 100 ppm in commercial poultry houses have also been reported (Anderson et al., Poult. Sci. 43: 305–318 (1964)).

Anderson et al. demonstrated that when chickens, turkeys, guinea pigs, or mice were exposed continuously to 20 ppm ammonia, gross or histopathological signs of damage to the respiratory tract occurred after six weeks (Avian Dis. 8:369–379, 1964). They also found that chicks exposed to 20 ppm ammonia for 72 hours were much more susceptible to Newcastle Disease than controls reared in ammonia-free environments. Although all of the chickens had been exposed to the Newcastle Disease virus, only 40% of the chickens in the ammonia-free environment were infected, whereas 100% of the chicks were infected when exposed to ammonia. They indicated that these results may have been due to damage to the mucous lining of the respiratory tract.

High levels of ammonia have been shown to enhance the multiplication of *Mycoplasma gallisepticum* in the respiratory tract of chickens (Sato et al., *Natl. Inst. Anim. Hlth. Qt.*, Tokyo, 13:45–53, 1973).

Charles et al. (*British Poultry Science* 7:177–187, 1966) found that keratoconjunctivitis developed in hens exposed to 100 ppm ammonia after six weeks, and egg production was depressed. Similarly, Strombaugh et al. found that high levels of ammonia adversely affected feed consumption and weight gain in pigs (*J. Anim. Sci.* 28:844, 1969).

In Europe, COSSH (Control of Substances Hazardous to Health) has set the limit of human exposure to ammonia at 25 ppm for an eight hour day and 35 ppm for a 10 minute exposure (Williams, *Proc. Ark. Nutrition Conference*, Fayetteville, Ark., pp. 14–29, 1992). With current production practices, these levels are often exceeded in broiler houses.

The number one complaint received by state and federal environmental agencies each year against animal producers involves odor. Since ammonia comprises a large portion of the odor associated with poultry litter, measures to control odor must incorporate strategies that reduce ammonia volatilization.

There are several litter amendments currently on the market which supposedly reduce ammonia volatilization. Among these are MLT (Multi-Purpose Litter Treatment), PLT (Poultry Litter Treatment), De-odorase, and Ammonia Hold. However, there are no published reports based on valid scientific studies in which these products were tested. Most of the products depend on testimonials from individuals for their sales. Further, it appears that at least two of these products contain nothing more than snake oil, which is clearly a waste of money for poultry producers. A need, therefore, exists for reproducible studies comparing these products with other compounds, which based on their chemical or physical properties, would likely reduce volatilization.

In addition to the ammonia volatilization, another major problem commonly associated with poultry litter is the amount of phosphorus (P) runoff which enters the aquatic system from fields receiving poultry litter. Phosphorus runoff is the primary cause for eutrophication in lakes and other freshwater bodies. Tighter controls of point sources of phosphorus, such as municipal waste water treatment plants, have resulted in decreased phosphorus loading from point sources into the aquatic environment in the last few decades. However, improvement of water quality has not always been observed when point source phosphorus loads were reduced. Therefore, attention is currently being focused on non-point sources of phosphorus such as agricultural runoff. One of the major sources of phosphorus runoff from agricultural lands is animal waste.

Several investigators have characterized phosphorus runoff from fields receiving poultry manure (Edwards et al., *J. Environ. Qual.* 22:361–365, 1993; McLeod et al., *J. Environ. Qual.* 13:122–126, 1984; Westerman et al., In (R. J. Smith, ed.) *Livestock waste: A renewable resource. Proc. Fourth Int. Symp. on Livestock Wastes,* 289–292. St. Joseph, Mich.:ASAE, 1980; and Westerman et al., *Transactions of the ASAE* 26:1070–1078, 1983). These studies have all shown that phosphorus runoff increases as the manure or litter application rate increases and as rainfall intensity increases. Drying time has also been shown to be an important parameter with respect to phosphorus runoff. With longer periods between application and rainfall, phosphorus runoff was greatly reduced (Westerman et al., supra, 1980; Westerman et al., supra, 1983). Recent studies have shown high concentrations of phosphorus (14–76 mg $PL^{-1}$) in runoff from pastures receiving poultry litter, most of which is dissolved inorganic phosphorus ($\approx 85\%$), with only small amounts of particulate phosphorus (Edwards et al., supra). Sonzogni et al. found that dissolved inorganic phosphorus is directly available to algae and concluded that best management practices used to decrease phosphorus runoff should consider the bioavailable-phosphorus load, rather than focusing on the total-phosphorus load (*J. Envir. Qual.* 11:555–563, 1982).

Rapid and concentrated growth of the poultry industry, fueled by the demand for low-fat meat, has raised concerns in several states regarding water quality. Arkansas, for example, is the number one poultry producing state in the U.S., with approximately one billion broilers produced per year. Each broiler produces approximately. 1.5 kg of poultry litter over a 10-week growing cycle (Perkins et al., *Bull.* NS 123, Georgia Agri. Exp. Station, Athens, Ga., 1964). This litter contains 8–25.8 g P $kg^{-1}$, with soluble reactive phosphorus levels up to 4.9 g P $kg^{-1}$ (Edwards et al., *Bioresource Tech.* 41:9–33, 1992). Runoff of phosphorus from fields receiving poultry litter has been speculated to be one of the primary factors affecting water quality in Northwest Arkansas, High bacterial counts and high biochemical oxygen demands have also been attributed to litter.

Currently, there is a movement to limit the amount of chickens produced in a given area to minimize phosphorus loading into the aquatic system. In the next 5 years, the U.S. Environmental Protection Agency will require all farms that produce in excess of 15,000 birds per year to construct detention ponds capable of holding all the runoff from a 25 year storm. As an alternative, poultry producers could be forced to transport litter to areas with low soil phosphorus and/or build litter storage facilities at a significant cost to poultry producers, and ultimately the consumer. An alternative solution is clearly needed to reduce soluble phosphorus levels in poultry litter.

SUMMARY OF THE INVENTION

The present invention is predicated on the discovery that treatment of poultry litter with the aluminum sulfate compound, alum, dramatically reduces ammonia volatilization from the litter. Results also indicate that alum, ferrous sulfate and calcium hydroxide effectively precipitate soluble phosphorus when added to litter, thereby reducing soluble phosphorus levels. Poultry litter is composed of a mixture of bedding material, manure, spilled food and feathers.

To inhibit ammonia volatilization, alum is applied to poultry litter in an amount sufficient to maintain the litter pH at values low enough to inhibit ammonia volatilization. Since poultry litter is highly variable in composition, the actual quantity of alum needed to inhibit volatilization may vary between approximately 5–25% of the litter weight on a dry weight basis.

To reduce phosphorus solubility in poultry litter in accordance with the present invention, aluminum, iron or calcium amendments were added to the poultry litter in an amount equivalent to a metal to phosphorus mole ratio of approximately 0.5:1 to 2.5:1. The most effective compounds reducing phosphorus solubility in litter include alum, ferrous and ferric sulfate, ferrous and ferric chloride, and calcium hydroxide.

Currently, over half of the nitrogen in poultry litter is lost via ammonia volatilization before it can be taken up by forages. This results in a poorly balanced fertilizer source, because the nitrogen/phosphorus ratio is low. Since forages have much higher requirements for nitrogen than phosporus, the best fertilizers should reflect this balance. Since the addition of alum acts to reduce volatilization losses, litter treated with alum would function as a higher quality fertilizer than those currently available on the market.

With respect to the environmental impact of these chemical amendments to litter (i.e., toxicity to the land and animals subject to runoff from fields treated with the chemicals), aluminum represents one of the primary components of soils and sediments. Its bio-availability is controlled by pH. Aluminum is non-toxic to plants and fish under normal pH conditions, for example, when soil pH is above about 4.5 and water pH is above pH 5.5.

In one embodiment for the treatment of litter, alum is applied to litter in an amount equivalent to approximately 5–25% of the litter weight on a dry weight basis.

In another embodiment, litter is treated with alum prior to field application.

Additional features and advantages of the present invention are further described, and will be apparent from the detailed description from the preferred embodiments.

DETAILED DESCRIPTION OF THE PREFERRED EMBODIMENTS

Figure 1:
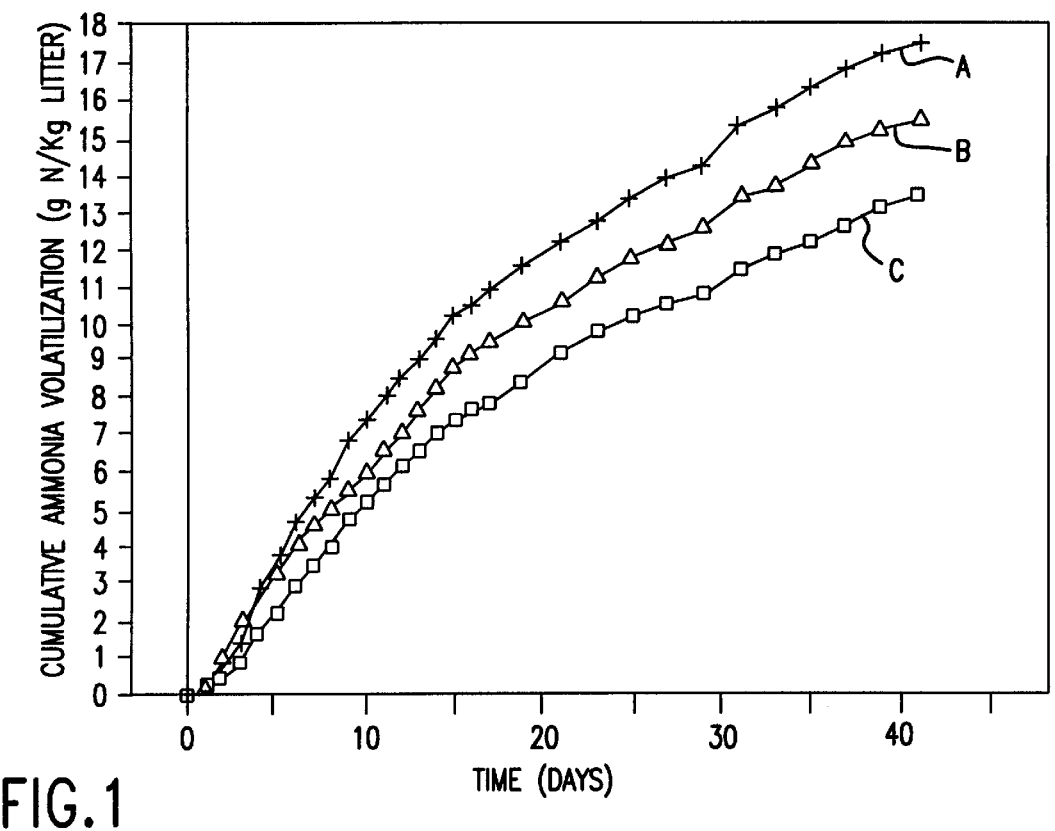
FIG. 1 illustrates cumulative ammonia volatilization (g nitrogen (N)/kg litter) from poultry litter with and without MLT amendments as a function of time (days). Plot A represents 10 g MLT. Plot B represents 20 g MLT. Plot C represents the control or unamended litter.

The present invention provides a method for treating poultry litter, which inhibits ammonia volatilization from the litter and reduces soluble phosphorus levels in the litter. The method involves the addition of alum to poultry litter. Alum is an aluminum sulfate compound having the composition $Al_2(SO_4)_3 \cdot nH_2O$, with n varying from approximately 14–18 molecules of water due to the varying degree of hydration in alum. Since poultry litter is highly variable in composition, the quantity of alum needed to arrest volatilization also varies. However, the amount of alum necessary to inhibit the buildup of atmospheric ammonia in poultry rearing facilities is the amount sufficient to maintain the litter pH at values low enough to inhibit ammonia volatilization. In this regard, alum is applied to the litter in an amount equivalent to approximately 5–25% of the litter weight on a dry weight basis. For example, 130 grams of alum would be applied per kilogram of litter. During a normal growout, 20,000 chickens will generate 20 tons of moist litter (16 tons dry). Therefore, 2 tons of alum would be required per poultry house after each growout.

Preferably, alum should be applied to the top of the litter and thoroughly mixed in with a mechanical mixer such as a power-tiller. Alum applications to litter also greatly reduced nitrogen loss in the litter, thereby further enhancing the value of this treated poultry litter as a fertilizer source. Ferrous sulfate was also found to dramatically reduce ammonia volatilization in litter.

Studies revealed that in addition to aluminum compounds like alum, calcium and iron compounds when added to poultry litter, precipitate the phosphorus in the litter, resulting in a reduction of water soluble phosphorus levels by as much as 99%. In this regard, water soluble phosphorus levels in poultry litter were reduced from over 2,000 mg phosphorus $kg^{-1}$ litter to less than 1 mg phosphorus $kg^{-1}$ litter with the addition of alum, quick lime, slaked lime, ferrous chloride, ferric chloride, ferrous sulfate and ferric sulfate under favorable pH conditions. To achieve a reduction in the soluble phosphorus levels in litter, alum, calcium, and iron compounds were applied to litter in an amount equivalent to having a mole ratio of the metal to phosphorus of approximately 0.5:1 to 2.5:1. These results along with actual field application studies suggest that treating litter prior to field application with these compounds could significantly reduce the amount of soluble phosphorus in runoff from litter-amended pastures and increase forage yields.

Although the methods of the present invention for treating litter focuses on poultry litter, it is contemplated that the addition of various compounds described herein would be applicable to other types of animal manures.

By way of example, and not limitation, the following examples serve to further illustrate the present invention in its preferred embodiments.

EXAMPLE 1

Experiment 1

(A) Methods and Materials

A laboratory study was conducted to determine if ammonia volatilization could be inhibited with chemical amendments. 92 g of fresh poultry litter (50 grams dry weight equivalent) was weighed into 44 air-tight plastic containers. 11 treatments were utilized in this study. The treatments were as follows:

1. control—litter alone
2. 25 g $Ca(OH)_2$ per kg litter
3. 50 g $Ca(OH)_2$ per kg litter
4. 100 g $Al_2SO_4$ 18 $H_2O$ per kg litter
5. 200 g $Al_2SO_4$ 18 $H_2O$ per kg litter
6. 100 g $Al_2SO_4$ 18 $H_2O$+50 g $CaCO_3$ per kg litter
7. 200 g $Al_2SO_4$ 18 $H_2O$+50 g $CaCO_3$ per kg litter
8. 100 g $FeSO_4$ 7 $H_2O$ per kg litter
9. 200 g $FeSO_4$ 7 $H_2O$ per kg litter
10. 10 g MLT per kg litter
11. 20 g MLT per kg litter There were 4 replications per treatment. The treatments were mixed into the litter. The containers were equipped with air inflows and outflows. Ammonia-free air was passed through each chamber and any ammonia volatilized from the litter was trapped in 30 ml of boric acid solution. At each sampling period, the boric acid was removed and titrated with 0.10 N HCl to determine the ammonia content. After the titration, the flasks were replaced with fresh boric acid solutions. Samples were titrated daily for the first 19 days and every other day thereafter. The study was carried out for 42 days.

At this time, a 20 gram sub-sample of the litter was extracted with 200 ml of deionized water for two hours. The samples were centrifuged at 6,000 RPM and aliquots were taken for pH, electrical conductivity (EC), alkalinity, ammonium, nitrate, soluble reactive phosphorus (SRP) and metals. Samples for EC, pH and alkalinity were unfiltered and were analyzed immediately. Samples for ammonium and nitrate were filtered through 0.45 $\mu$m filter and frozen. Metal and SRP samples were filtered (0.45 $\mu$m), acidified to pH 2.0 with ultrapure $HNO_3$, and frozen. Total dissolved phosphorus and metals were determined by ICAP (inductively coupled argon plasma emission spectrometer). Soluble reactive phosphorus was determined using an autoanalyzer. After the water extract, the litter was extracted with 1 N KCl for 2 hours for exchangeable ammonium. After centrifuging, these samples were filtered and analyzed for ammonium. 10 gram sub-samples were taken from each container for water content and TKN (total kjeldahl nitrogen) analysis. Total nitrogen was determined by kjeldahl distillation. Fecal coliform counts were made on litter samples taken at this time and were analyzed by the Arkansas Water Resources Laboratory using the most probably number method. All samples tested negative for fecal coliform.

(B) Results

As shown in FIG. 1, an average of 13.2 g N $kg^{-1}$ litter was lost from the controls (unamended litter) during the 42 day incubation period. This corresponds to an $NH_3$ volatilization rate of 314 mg N $kg^{-1}$ $day^{-1}$. Applications of MLT actually increased $NH_3$ volatilization. The recommended rate (10 g MLT $kg^{-1}$) resulted in 31% more N loss via volatilization than the controls. At 2 times the recommended rate (20 g MLT $kg^{-1}$), volatilization was 15% higher than the controls. These results are not surprising, since the pH of MLT and water is around 10. Increases in litter pH shift the $NH_3/NH_4$ equilibrium towards $NH_3$, resulting in higher volatilization.

Figure 2:
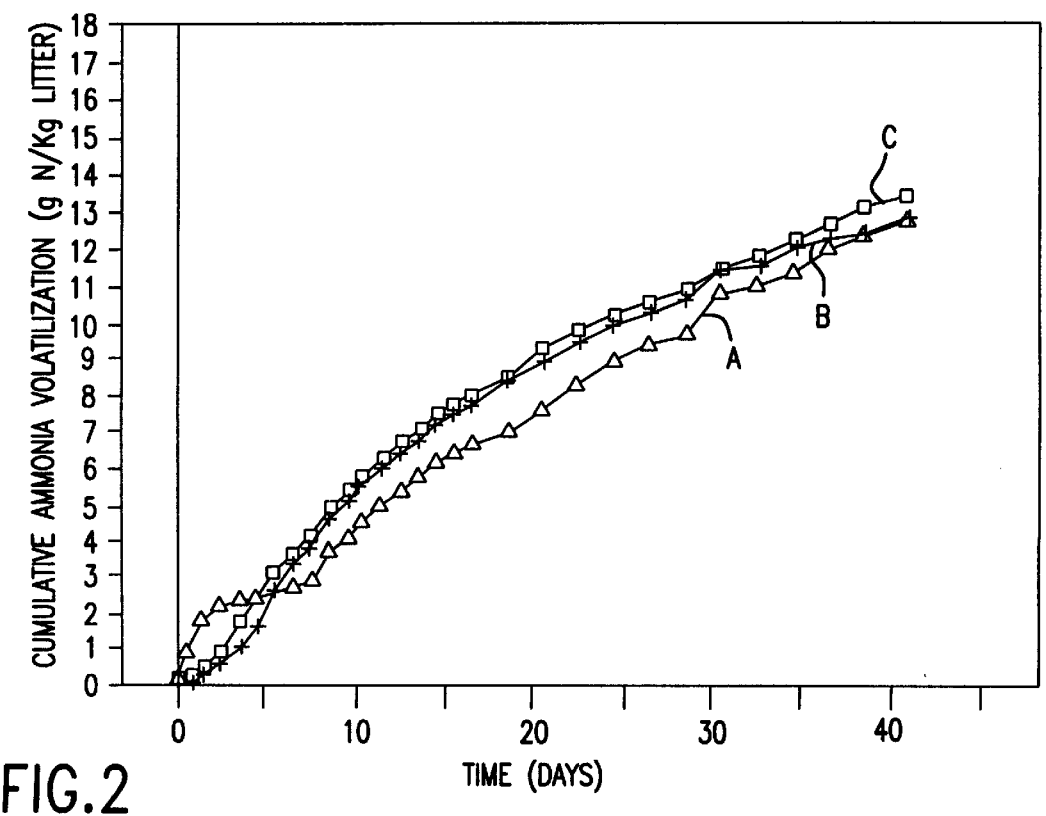
FIG. 2 illustrates cumulative ammonia volatilization (g N/kg litter) from poultry litter with and without calcium hydroxide amendments as a function of time (days). Plot A represents 50 g Ca(OH)$_2$. Plot B represents 25 g Ca(OH)$_2$. Plot C represents the control or unamended litter.

As shown in FIG. 2, ammonia volatilization from litter treated with $Ca(OH)_2$ was not significantly different from that in the controls. During the first three days of the experiment, the rate of $NH_3$ loss from the 50 g $Ca(OH)_2$ $kg^{-1}$ treatment was much faster than the controls, which was probably due to increases in pH. However, $Ca(OH)_2$ was probably converted to $CaCO_3$ with time, resulting in lower pHs. The pHs of the $Ca(OH)_2$ treatments were not significantly different from the controls after 42 days of incubation.

Figure 3:
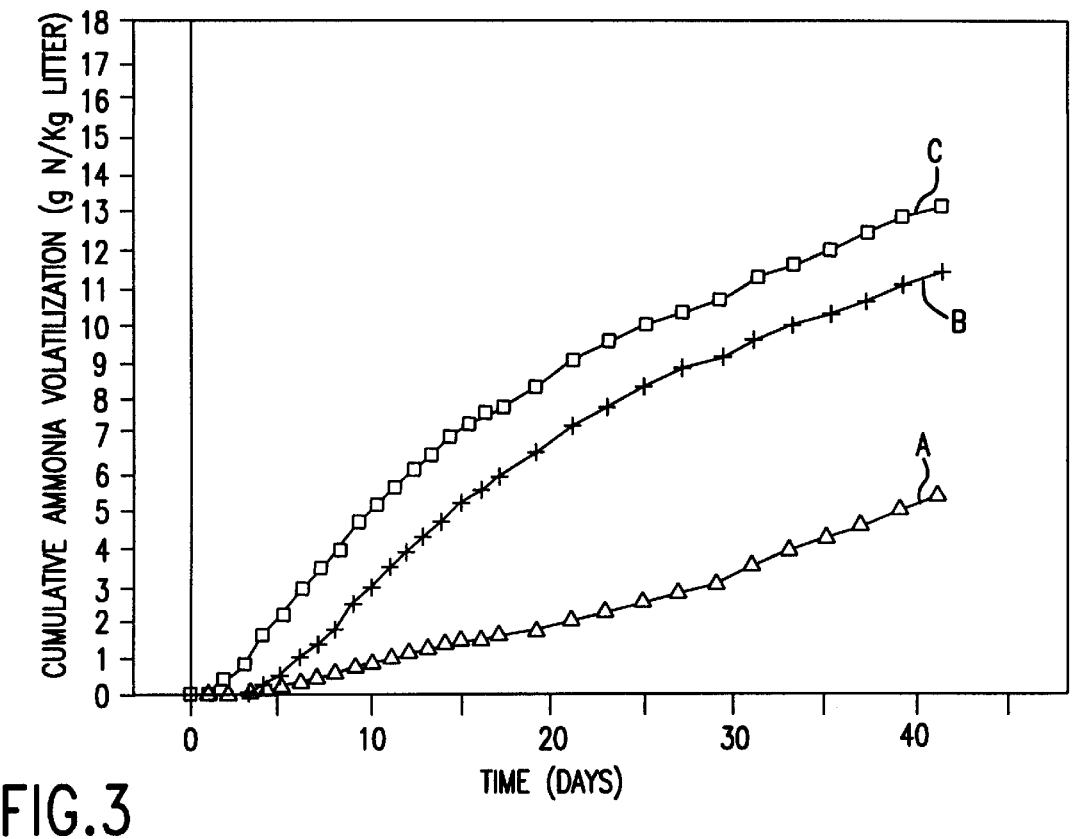
FIG. 3 illustrates cumulative ammonia volatilization (g N/kg litter) from poultry litter with and without ferrous sulfate amendments as a function of time (days). Plot A represents 200 g FeSO$_4$. Plot B represents 100 g FeSO$_4$. Plot C represents the control or unamended litter.

Applications of $FeSO_4 \cdot 7 H_2O$ decreased $NH_3$ volatilization. This is illustrated in FIG. 3. Cumulative $NH_3$ losses were 12 and 58% lower than the controls for the 100 and 200 g $FeSO_4 \cdot 7 H_2O$ $kg^{-1}$ treatments, respectively. This is probably due to a decrease in litter pH, since $FeSO_4 \cdot 7 H_2O$ is an acid forming compound.

Figure 4:
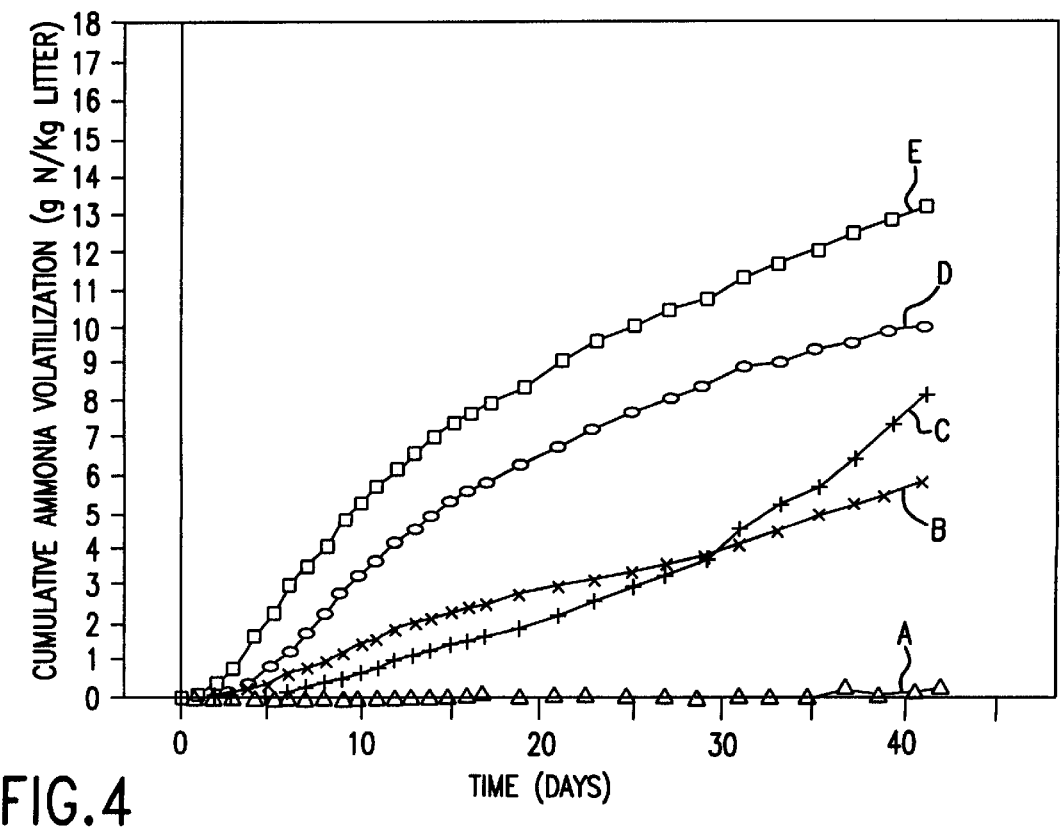
FIG. 4 illustrates cumulative ammonia volatilization (g N/kg litter) from poultry litter with and without aluminum sulfate amendments as a function of time (days). Plot A represents 200 g alum. Plot B represents 200 g alum+CaCO$_3$. Plot C represents 100 g alum. Plot D represents 100 g alum+CaCO$_3$. Plot E represents the control or unamended litter.

As shown in FIG. 4, alum applications, both with and without $CaCO_3$, greatly reduced $NH_3$ volatilization. Nitrogen losses with alum in combination with 100 g $CaCO_3$ were 24 and 57% lower than the controls at the 100 and 200 g alum $kg^{-1}$ rates, respectively. When alum was applied alone, the N loss was greatly reduced, with cumulative $NH_3$ losses 38 and 99% lower than the controls for the 100 and 200 g alum $kg^{-1}$ treatment, respectively. In fact, only 0.2 g N $kg^{-1}$ were lost due to $NH_3$ volatilization at the high rate of alum, and this occurred in the last week of the study. Prior to that time, $NH_3$ loss from the 200 g alum $kg^{-1}$ treatment had been zero.

Figure 5:
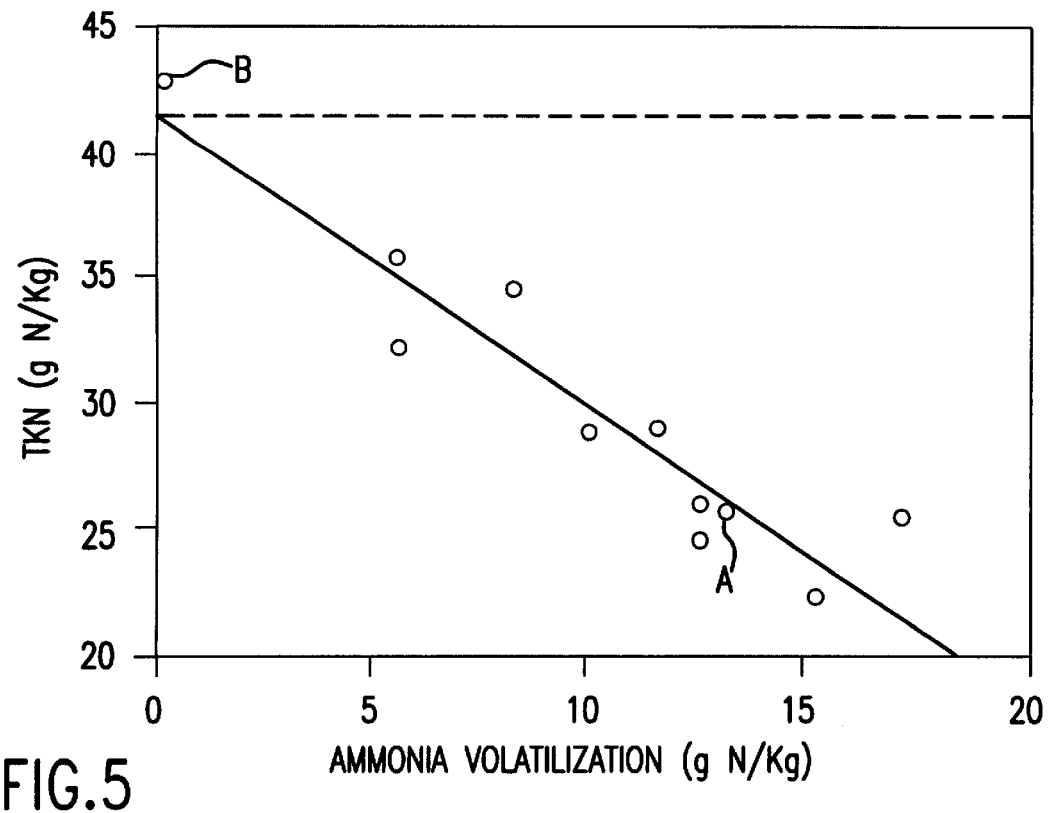
FIG. 5 illustrates total N content of the litter after 42 days of incubation as a function of the cumulative ammonia volatilization (g N/kg) from the various treatments in Experiment 1. Point A represents the control or unamended litter. Point B represents the total N content of the 200 g alum kg$^{-1}$ treatment. R is the regression coefficient with a value of 0.94. y=−1.17x+41.7.

In FIG. 5, the total N content of the litter after 42 days of incubation is plotted as a function of the cumulative $NH_3$ volatilization for the various treatments. Treatments with higher volatilization had lower total N contents at the end of the study as would be expected. The total N content of the 200 g alum $kg^{-1}$ treatment was 43 g N $kg^{-1}$. This is somewhat higher than the original N content (41.8 g N $kg^{-1}$). If the amount of alum present had been taken into account, then the N content would be 52.3 g N $kg^{-1}$. Higher total N contents as compared to the original N content are due to losses in carbon via $CO_2$ evolution from microbial decomposition. The controls contained 25.5 g N $kg^{-1}$ at the conclusion of the study. Therefore, the addition of alum at the higher rate resulted in a doubling of the N content in the litter. This would greatly increase the value of poultry litter as a fertilizer source.

EXAMPLE 2

Experiment 2

(A) Methods and Materials

In order to determine the relative effectiveness of the products currently being sold as $NH_3$ volatilization inhibitors, as well as ferrous sulfate and alum, a second study was conducted.

50 g (dry weight equivalent) of fresh poultry litter was weighed into 44 plastic containers. Different products were compared and rates of each were as follows:

|   | recommended rate | metric rate | cost/house |
|---|---|---|---|
| 1. control | 0 | 0 | 0 |
| 2. acid mine soil | 50 lb/100 $ft^2$ | 200 g/kg | ? |
| 3. aluminum sulfate | 50 lb/100 $ft^2$ | 200 g/kg | $880 |
| 4. ammonia hold | 1 lb/100 $ft^2$ | 4 g/kg | $288 |
| 5. brown mud | 50 lb/100 $ft^2$ | 200 g/kg | ? |
| 6. de-odorase | 4 oz/100 $ft^3$ | 0.52 ml/kg | ? |
| 7. ferrous sulfate | 50 lb/100 $ft^2$ | 200 g/kg | $420 |
| 8. FBC | 30 lb/100 $ft^2$ | 120 g/kg | ? |
| 9. MLT | 1 gal/480 $ft^2$ | 6.95 ml/kg | ? |
| 10. PLT | 5 lb/100 $ft^2$ | 20 g/kg | $280 |
| 11. red mud | 50 lb/100 $ft^2$ | 200 g/kg | ? |

Rates were based on a house size of 16,000 $ft^2$, containing 20 tons litter. There were 4 replications per treatment in a completely randomized design. The containers were equipped with air inflows and outflows. Ammonia-free air was passed through each chamber and any ammonia volatilized from the litter was trapped in two 50 ml volumetric flasks containing 30 ml of boric acid solution. At each sampling period, the boric acid was removed and titrated with 0.10 N HCl to determine the ammonia content. After the titration, the flasks were replaced with fresh boric acid solutions. Sampling times were daily for the first 21 days and every 2 days thereafter. After 42 days, a 20 gram sub-sample of the litter was extracted with 200 ml of deionized water for 2 hours. The samples were centrifuged at 6,000 RPM and aliquots were taken for pH, EC, alkalinity, ammonium, nitrate, SRP and metals. Analyses were conducted as described above in Experiment 1.

(B) Results

Figure 6:
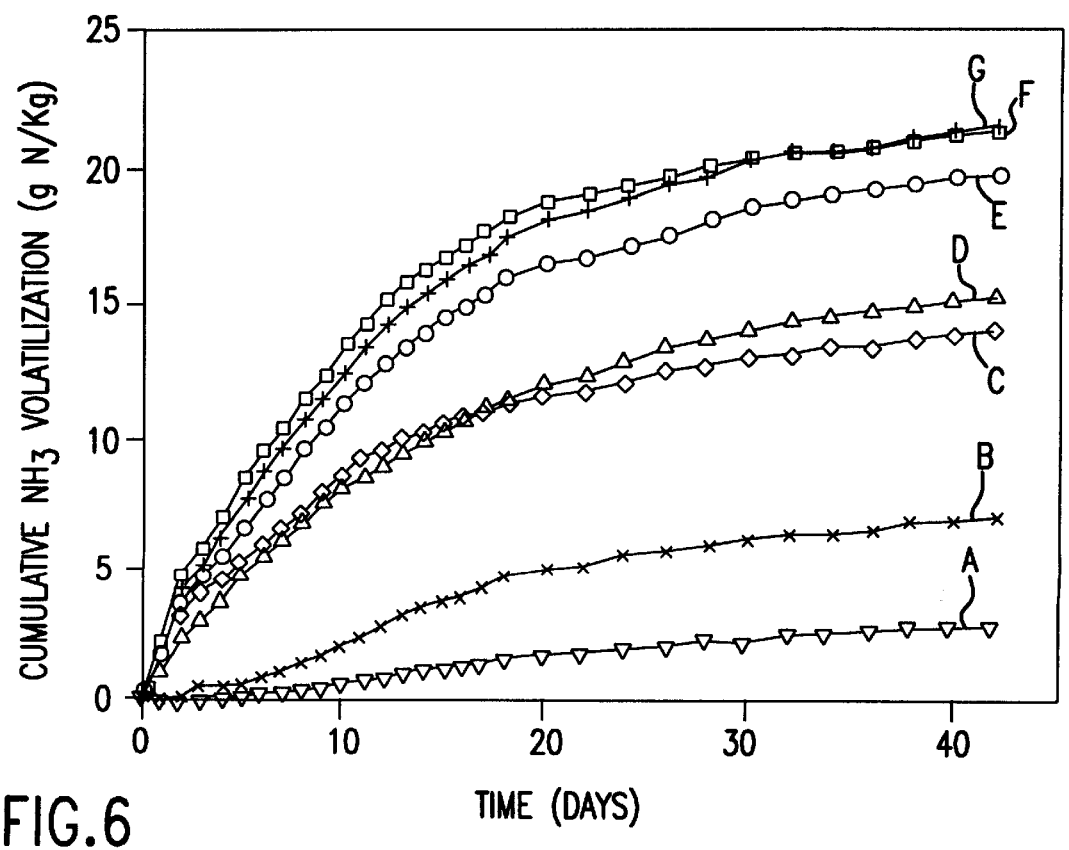
FIG. 6 illustrates cumulative ammonia volatilization (g N/kg) from poultry litter with and without various chemical amendments as a function of time (days). Plot A represents alum. Plot B represents ferrous sulfate. Plot C represents ammonia hold. Plot D represents PLT. Plot E represents the control. Plot F represents MLT. Plot G represents De-odorase.

As shown in FIG. 6, ammonia volatilization from litter treated with MLT was 8% higher than the controls. These results confirm those found in Experiment 1 and indicate that this product, which is currently being sold in several states, increases rather than decreases $NH_3$ volatilization. De-odorase, a product made from yucca plant extract, also increased volatilization (9% more N loss than the controls).

The only two commercial products that appeared to work at all were Ammonia Hold and PLT, which reduced N losses by 29 and 23%, respectively, as compared to the controls. However, reduction in $NH_3$ volatilization was much greater with ferrous sulfate and alum, which resulted in 65 and 85% less N loss, respectively. These data indicate that these two treatments are far better than what is currently available commercially.

In Table 1 below, the cost of treating an average poultry house for one growout with these amendments is provided. In order to make a proper comparison, the products' effectiveness must be taken into account. This was done by calculating the cost to treat an average house (20 tons of litter) and dividing that by the amount of N conserved by each treatment. These data indicate that alum and ferrous sulfate are much more cost effective than the best commercial product that was found to inhibit volatilization.

TABLE 1

Cost and cost-effectiveness of various poultry litter amendments. Cost are based on recommended rates for one growout in a 16,000 $ft^2$ house.

| amendment | cost/house | amount N conserved≠ (lbs N/house) | cost/lb N held |
|---|---|---|---|
| ferrous sulfate | $420 | 957 | $9.44 |
| alum | $880 | 1112 | $0.79 |
| Ammonia Hold | $288 | 28 | $10.15 |
| PLT | $280 | 42 | $6.63 |

TABLE 1-continued

Cost and cost-effectiveness of various poultry litter amendments. Cost are based on recommended rates for one growout in a 16,000 ft² house.

| amendment | cost/house | amount N conserved≠ (lbs N/house) | cost/lb N held |
|---|---|---|---|
| MLT | | increases NH₃ volatilization | |
| De-odorase | | increases NH₃ volatilization | |

PLUS CODE 116 IS NOT DEFINEDAmount N conserved was calculated based on the increase in nitrogen content of litter above that observed in the control samples, assuming 40,000 lbs litter are produced per growout.

It should be noted that alum and ferrous sulfate would be more desirable than Ammonia Hold and PLT from an environmental point of view, since they would immobilize soluble phosphorus in the litter. On the other hand, phosphoric acid is used to produce Ammonia Hold. This would result in higher phosphorus loading onto the land, resulting in higher phosphorus runoff. Poultry litter treater (PLT) is composed of $NaHSO_4$. This compound reduces litter pH (which solubilizes calcium phosphates), without providing a phosphate binding agent, like Al, Ca and/or Fe.

Figure 7:
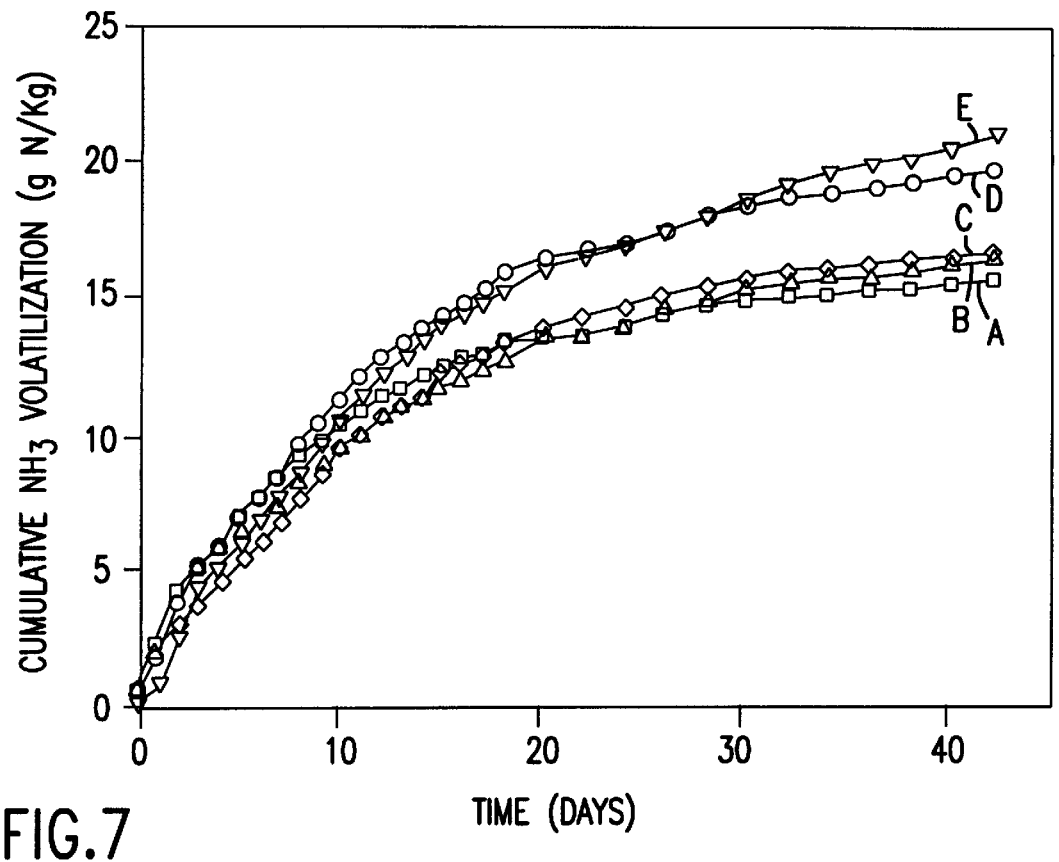
FIG. 7 illustrates cumulative ammonia volatilization (g N/Kg) from poultry litter with and without various waste products as a function of time (days). Plot A represents red mud. Plot B represents FBC (fluidized bed combustion material). Plot C represents brown mud. Plot D represents the control. Plot E represents acid mine soil.

As shown in FIG. 7, cumulative $NH_3$ volatilization from litter amended with acid mine soil was roughly equivalent of that of the controls. Brown mud and red mud, two clay wastes from aluminum processing in Arkansas reduced volatilization by 15 and 20%, respectively. Similarly, fluidized bed combustion material (FBC), a waste product from coal-fired power plants, reduced volatilization by 16%. All of these waste products should theoretically reduce soluble phosphorus levels in poultry litter. Future studies will also be conducted to determine if increasing rates of these amendments will decrease volatilization.

Figure 8A:
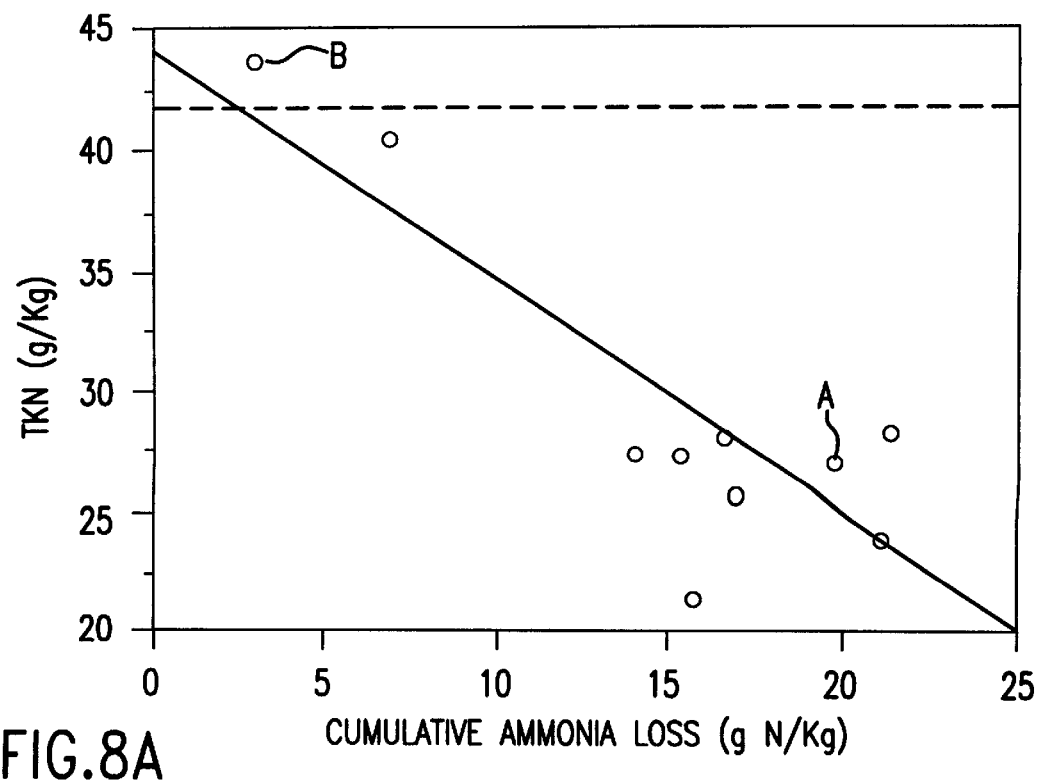
FIG. 8A illustrates total N content of the litter after 42 days of incubation as a function of the cumulative ammonia volatilization (g N/kg) from the various treatments in Experiment 2. Point A represents the control. Point B represents the alum treated litter. The original nitrogen content is 41.8 g/kg. R is the regression coefficient with a value of 0.84. y=−0.96x+44.1.

Total kjelkdahl N (TKN) in the litter at the conclusion of Experiment 2 is plotted as a function of cumulative ammonia volatilization in FIG. 8. Decreases in TKN were observed in samples that had higher volatilization rates, while TKN increased in the alum and ferrous sulfate treated litter. The reasons for this increase are the same as those noted for Experiment 1.

The rate of ammonia volatilization is dependent on pH, moisture content, wind speed, ammonium concentration and temperature. Volatilization increases with increases in any of these variables. The pH of litter is very important because it determines the ratio of $NH_3/NH_4$. As pH increases, this ratio increases, causing volatilization to increase and vice versa. Therefore, acid forming compounds, like alum and ferrous sulfate, reduce volatilization, whereas basic compounds like MLT (which has a pH of 10) increases volatilization.

Results from this study indicate that alum and ferrous sulfate greatly reduce ammonia volatilization from poultry litter. By decreasing nitrogen losses from volatilization, the use of these products results in a higher total nitrogen content in poultry litter, thus increasing the value of the litter as a fertilizer. These compounds, which have also been shown to immobilize phosphorus in litter, are cheaper and more effective than any commercial products currently available. Since high ammonia levels in poultry houses cause major economic losses to producers, the use of these compounds should result in increased profitability to producers, while simultaneously decreasing the negative environmental impact from land application of poultry litter.

EXAMPLE 3
Determination of Alum Requirement in Poultry Litter for Inhibition of Ammonia Volatilization The objective of this study was to determine the amount of alum needed to inhibit volatilization from litter. Rather than measure ammonia volatilization, litter pH was used as an indicator of whether or not volatilization would occur. Based on the two previous studies, it was determined that the target pH to inhibit volatilization was approximately 5.75 for the methods being used to determine pH.

Broiler litter was obtained from 3 low ventilation environmental chambers and 8 commercial broiler houses, all of which had at least 2 growouts on the litter. The litter from the 3 chambers was composited and 20 grams moist litter from each source was weighed into 250-ml polycarbonate centrifuge tubes. There were 6 treatments: 0, 1, 2, 3, 4, and 5 g alum/20 g moist litter. After adding the alum to the litter, 200 ml of deionized water was added to each tube, which was then shaken for 2 hours. The pH of the supernatant was then determined. Water content was determined on each litter source in order to convert rates to a dry weight basis.

Figure 8B:
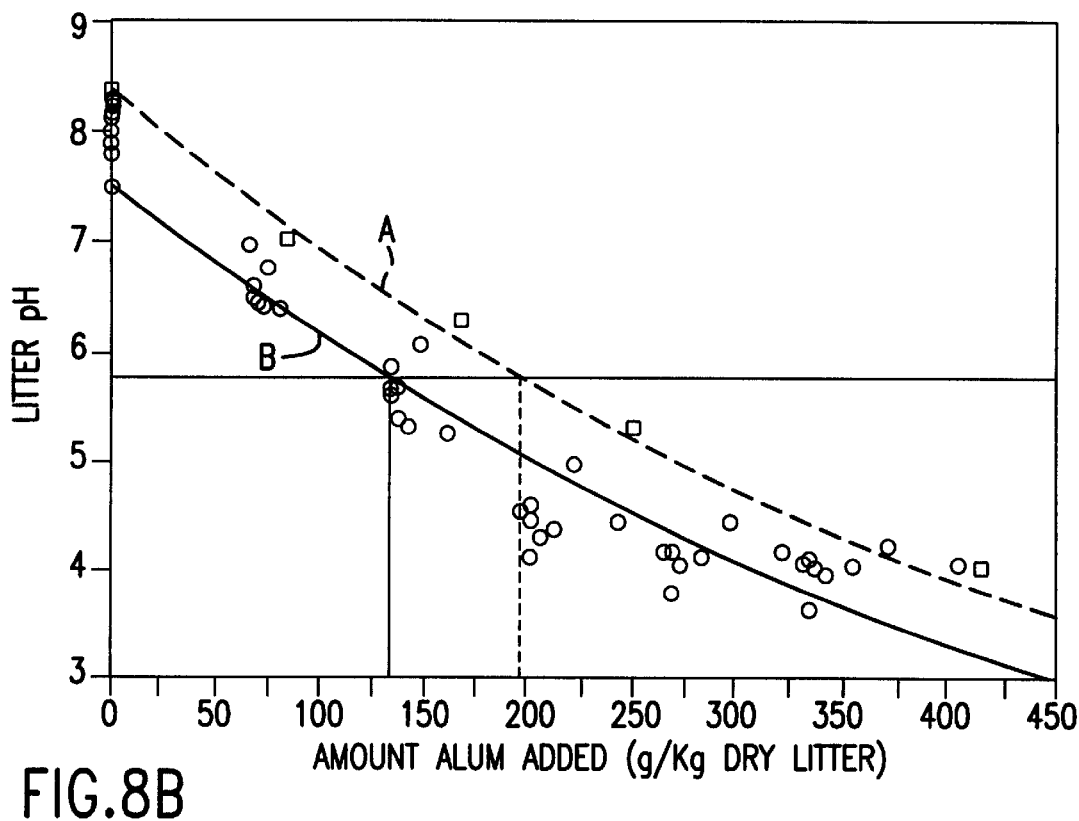
FIG. 8B illustrates the amount of alum added to poultry litter for inhibition of ammonia volatilization as a function of litter pH. Plot A represents litter from low ventilation environmental chambers. Plot B represents litter from eight commercial broiler houses.

As shown in FIG. 8B, alum additions resulted in decreases in pH of the litter from both the commercial houses and environmental chambers. However, the amount of alum needed to reach pH 5.75, or inhibit ammonia volatilization, was much lower in litter from commercial houses as compared to the litter from the environmental chambers (130 versus 200 g/kg dry litter). There is approximately 20 tons of moist litter produced in a growout (16 tons dry). Therefore, the alum requirement for a commercial house would be approximately 2 tons per growout. Assuming alum can be purchased for $220/ton, the cost of treating a commercial broiler house is approximately $440.

EXAMPLE 4

(A) Methods and Materials

The objective of this study was to determine if soluble phosphorus levels could be reduced in poultry litter with aluminum (Al), calcium (Ca), and/or iron (Fe) amendments.

To this end, 26 grams of fresh poultry litter (20 grams dry weight equivalent) were weighed into glass bottles. The litter had been forced through a 10 mesh sieve to break up large clumps and mixed in a portable cement mixer for 2 hours to insure homogeneity. The bedding of this litter was rice hulls. The litter had not been stacked or composed. The initial pH (1:1) and electrical conductivity (1:10, litter:water extract) was 8.2 and 8970 $\mu S\ cm^{-1}$, respectively. Total N, P, and Potassium (K) were 42.8, 18.1, and 27.3 g $kg^{-1}$, respectively. Total Kjeldahl N was determined on the fresh poultry litter according to the method of Bremner et al. In (A. L. Page, R. H. Miller and D. R. Keeney eds.) *Methods of Soil Analysis, Part 2, Second Edition.* Amer. Soc. Agron. Publ. Madison, Wis., 1982). Total phosphorus and potassium were determined on fresh litter using the method of Huang et al. (*Commun. in Soil Sci. Plant Anal.* 16:943–958, 1985).

The litter was amended with aluminum, calcium, and iron compounds to reduce phosphorus solubility. Materials tested included alum, sodium aluminate, quick lime, slaked lime, calcitic limestone, dolomitic limestone, gypsum, ferrous chloride, ferric chloride, ferrous sulfate and ferric sulfate. All amendments were reagent grade materials. After the amendments had been added, the mixtures were stirred with a spatula for approximately 1 minute. The calcium treatments were tested with and without $CaF_2$ additions as a secondary amendment in an attempt to precipitate fluorapatite. Calcium carbonate was added as a secondary amendment in cases where the primary amendment was believed to be an acid forming compound.

As shown below in Table 2, there were 20 different chemical treatments tested, with 5 rates of each treatment (total number of treatments equalled 100 plus control) and 3 replications. The lowest rate of the iron and aluminum amendments was equal to the amount needed to achieve a 1:1 metal:phosphorus mole ratio, assuming the phosphorus content of the litter was 10 mg kg$^{-1}$. The lowest rate of the calcium amendments was based on a calcium:phosphorus ratio of 1.5:1. It should be noted that while the rates were based on the assumption that the phosphorus content of litter was 10 mg phosphorus kg$^{-1}$, the actual phosphorus content was found to be 18.1 mg phosphorus kg$^{-1}$. Therefore, the lowest rate of aluminum and iron was equivalent to 1:1.8 mole ratio, etc. In view of these studies and based on the differences noted with the use of each of the aluminum, calcium, and iron compounds, the amount of each compound sufficient to reduce soluble phosphorus levels in poultry litter is equivalent to a metal to phosphorus mole ratio of approximately 0.5:1 to 2.5:1.

TABLE 2

Rates of chemical amendments utilized in this study.

| Treatment | rate of primary amendment | secondary |
|---|---|---|
| | g/kg litter | |
| 1. CaO | 30, 60, 90, 120, 150 | 0 |
| 2. CaO + CaF$_2$ | 30, 60, 90, 120, 150 | 5 |
| 3. Ca(OH)$_2$ | 40, 80, 120, 160, 200 | 0 |
| 4. Ca(OH)$_2$ + CaF$_2$ | 40, 80, 120, 160, 200 | 5 |
| 5. CaCO$_3$ | 50, 100, 150, 200, 250 | 0 |
| 6. CaCO$_3$ + CaF$_2$ | 50, 100, 150, 200, 250 | 5 |
| 7. CaMg(CO$_3$)$_2$ | 100, 200, 300, 400, 500 | 0 |
| 8. CaMg(CO$_3$)$_2$ + CaF$_2$ | 100, 200, 300, 400, 500 | 5 |
| 9. CaSO$_4$.2H$_2$O | 100, 200, 300, 400, 500 | 0 |
| 10. CaSO$_4$.2H$_2$O + CaF$_2$ | 100, 200, 300, 400, 500 | 5 |
| 11. Al$_2$(SO$_4$)$_3$.18H$_2$O | 100, 200, 300, 400, 500 | 0 |
| 12. Al$_2$(SO$_4$)$_3$.18H$_2$O + CaCO$_3$ | 100, 200, 300, 400, 500 | 100 |
| 13. Na$_2$Al$_2$O$_4$ | 25, 50, 75, 100, 125 | 0 |
| 14. Na$_2$Al$_2$O$_4$ + CaCO$_3$ | 25, 50, 75, 100, 125 | 100 |
| 15. Fe$_2$(SO$_4$)$_3$.2H$_2$O | 60, 120, 180, 240, 300 | 0 |
| 16. FeCl$_3$ | 50, 100, 150, 200, 250 | 0 |
| 17. FeSO$_4$.7H$_2$O | 90, 180, 270, 360, 450 | 0 |
| 18. FeSO$_4$.7H$_2$O + CaCO$_3$ | 90, 180, 270, 360, 450 | 100 |
| 19. FeCl$_2$.4H$_2$O | 60, 120, 180, 240, 300 | 0 |
| 20. FeCl$_2$.4H$_2$O + CaCO$_3$ | 60, 120, 180, 240, 300 | 100 |

After amendments were added to the litter, deionized water was added to achieve a water content of 20% by volume. The amended litter was then incubated in the dark at 25° C. for one week. A one week equilibration time was utilized for this study because this is usually the time scale between the removal of broilers from the houses after the final growout before litter removal and land application of the litter. At the end of this period, the litter was transferred to polycarbonate centrifuge tubes, shaken for 2 hours with 200 mL of deionized water, and centrifuged at 4066 g for 20 min. Unfiltered samples were collected for measurement of pH, alkalinity, and electrical conductivity (EC). Alkalinity was determined by titration, according to APHA method 2320 B (*American Public Health Association (APHA), Standard Methods for the Examination of Water and Wastewater.* 18 Ed. Amer. Publ. Health Assoc., Wash., D.C. pp. 1268, 1992). Filtered samples (0.45 µm millipore filters) were collected for measurement of soluble reactive phosphorus (SRP), water soluble metals (Al, B, Ca, Cu, Fe, K, Mg, Mn, Na, P, S, Zn), soluble organic carbon (SOC), SO$_4$, and Cl. The metal and SRP samples were acidified to pH 2.0 with nitric acid to prevent precipitation. Chloride, SOC, and SO$_4$ samples were not acidified. Soluble reactive phosphorus was determined using an ascorbic acid technique, according to APHA method 424-G (APHA, supra). Metals were analyzed using an inductively coupled argon plasma emission spectrometer (ICP), according to APHA method 3120 B (APHA, supra). Soluble organic carbon was determined as the difference between total organic carbon and inorganic carbon as measured on a Rosemont DC-190 organic carbon Analyzer, using the combustion-infrared method according to APHA method 5310 B (APHA, supra). Sulfate was determined using the turbidimetric method, according to APHA method 4500-SO$_4^2$ E (APHA, supra). Chloride was determined using the potentiometric method with a chloridometer, according to APHA method 4500-Cl$^-$ D (APHA, supra).

(B) Results (1) Calcium Amendments

As shown in FIG. 1, calcium oxide decreased the water soluble phosphorus levels in the litter from >2000 mg phosphorus/kg to <1 mg phosphorus/kg when an equivalent of 43 g calcium was added per kg of litter. It is not known whether this was due to precipitation or adsorption. Whatever the mechanism, the data suggest that soluble phosphorus runoff from fields receiving poultry litter could be decreased significantly if the litter were pretreated with CaO. The pH of the litter increased from 7.2 (control) to approximately 12 at the higher rates of CaO as shown in Table 3.

TABLE 3

Effect of Al, Ca and Fe compounds on pH of poultry litter.

| | Amendment Level (see Table 1 for actual rates) | | | | |
|---|---|---|---|---|---|
| Treatment | 1× | 2× | 3× | 4× | 5× |
| | pH units | | | | |
| control | 7.30 | | | | |
| CaO | 9.82 | 11.76 | 12.29 | 12.41 | 12.44 |
| CaO + CaF$_2$ | 9.71 | 11.38 | 12.24 | 12.40 | 12.45 |
| Ca(OH)$_2$ | 9.12 | 11.06 | 12.23 | 12.32 | 12.33 |
| Ca(OH)$_2$+ CaF$_2$ | 9.51 | 11.43 | 12.21 | 12.30 | 12.34 |
| CaCO$_3$ | 7.87 | 8.10 | 7.87 | 7.37 | 7.27 |
| CaCO$_3$+ CaF$_2$ | 6.88 | 7.64 | 7.75 | 7.56 | 7.65 |
| CaMg(CO$_3$)$_2$ | 7.69 | 7.35 | 7.84 | 8.24 | 7.98 |
| CaMg(CO$_3$)$_2$ + CaF$_2$ | 8.21 | 8.05 | 7.52 | 7.65 | 8.18 |
| CaSO$_4$.2H$_2$O | 7.41 | 7.57 | 7.36 | 7.68 | 7.32 |
| CaSO$_4$.2H$_2$O + CaF$_2$ | 7.36 | 7.14 | 7.43 | 7.61 | 7.32 |
| Al$_2$(SO$_4$)$_3$.18H$_2$O | 5.73 | 4.26 | 3.81 | 3.59 | 3.50 |
| AL$_2$(SO$_4$)$_3$.18H$_2$O + CaCO$_3$ | 7.56 | 6.75 | 6.46 | 5.37 | 4.18 |
| Na$_2$Al$_2$O$_4$ | 7.78 | 8.97 | 9.88 | 10.55 | 11.01 |
| Na$_2$Al$_2$O$_4$ + CaCO$_3$ | 7.97 | 9.31 | 10.31 | 10.56 | 11.18 |
| Fe$_2$(SO$_4$)$_3$.2H$_2$O | 7.21 | 4.86 | 2.77 | 2.45 | 2.33 |
| FeCl$_3$ | 5.33 | 3.52 | 2.21 | 1.97 | 1.88 |
| FeSO$_4$.7H$_2$O | 7.13 | 5.67 | 4.39 | 4.28 | 5.15 |
| FeSO$_4$.7H$_2$O + CaCO$_3$ | 6.76 | 6.17 | 6.03 | 6.14 | 5.21 |
| FeCl$_2$.2H$_2$O | 7.19 | 4.85 | 4.42 | 4.09 | 3.95 |
| FeCl$_2$.2H$_2$O + CaCO$_3$ | 7.32 | 6.23 | 6.05 | 5.83 | 5.34 |

(LSD.05 = 0.30)

A reduction in pH of the litter treated with CaO would be expected with time, due to equilibration with atmospheric CO$_2$. This gradual reduction in pH may result in increased phosphorus solubility, since the solubility of calcium phosphates is extremely pH dependent. However, even if the pH drops to 8, the equilibirum concentration of the most soluble calcium phosphate minerals, such as brushite (CaHPO$_4$·2H$_2$O), would be about 10$^{-4}$ M or 3 mg p L$^{-1}$ (Lindsay, *Chemical Equilibria in Soils.* 449 pp. John Wiley & Sons, N.Y.). This would still be roughly 2 orders of magnitude lower than soluble phosphorus levels determined for the litter used (200 mg P L$^{-1}$).

Recently, it has been determined that the majority of phosphorus runoff from land application of poultry manure occurs during the first runoff event (Edwards et al., *J. Environ. Qual.* 22:361–365, 1993). If soluble phosphorus levels could be decreased for at least a few weeks following land application, then there would be time for precipitation and adsorption by soils to occur, as well as uptake by plants and microorganism. Therefore, if the solubility of phosphorus was lowered for only a short period of time, it would be beneficial from both an environmental and an agronomic viewpoint.

Figure 9:
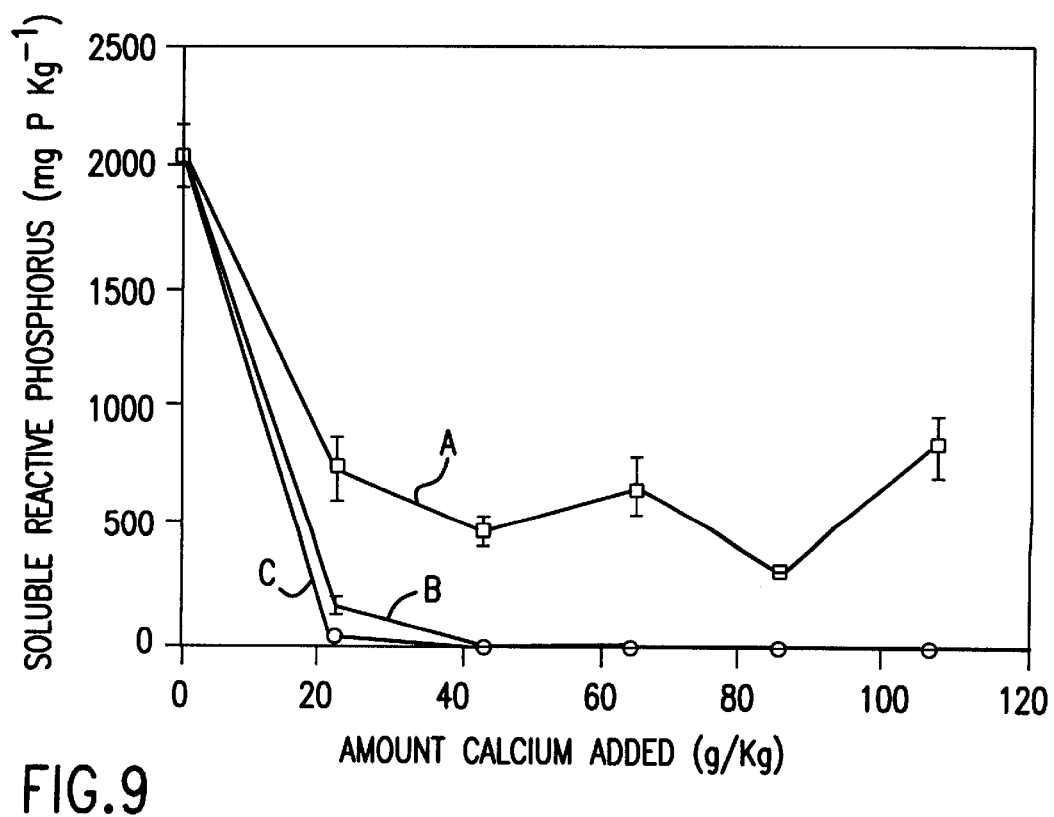
FIG. 9 illustrates the effective calcium amendments to poultry litter on water soluble reactive phosphorus. Plot A represents gypsum. Plot B represents calcium hydroxide. Plot C represents calcium oxide.

Calcium hydroxide decreased phosphorus solubility in poultry litter in the same manner as CaO. This is shown in FIG. 9. Since $Ca(OH)_2$ is less caustic, this treatment would be preferable to CaO, which can cause severe burns upon skin contact.

Calcitic and dolomitic limestone on phosphorus solubility in poultry litter had very little effect on SRP concentrations. There are several possible reasons why these amendments did not work. One possibility is that the experiment was not carried out for a sufficient period of time. Normally, it takes months for limestone to completely react and neutralize soil acidity. Our incubation period was one week, which may have been an insufficient time perod for solubilization and precipitation reactions. Phosphorus adsorption by calcite should have occurred, since this is an extremely fast reaction.

The pH of the unamended litter was initially 8.2, which decreased to 7.2 after one week. Both calcite and dolomite are relatively insoluble at this pH, which may have led to inadequate amounts of $Ca^{2+}$ in solution to precipitate the phosphorus. However, even if the $Ca^{2+}$ concentrations in solution were low, phosphorus adsorption onto the calcite surface should have removed phosphorus from solution based on research previously done in this area.

Figure 10:
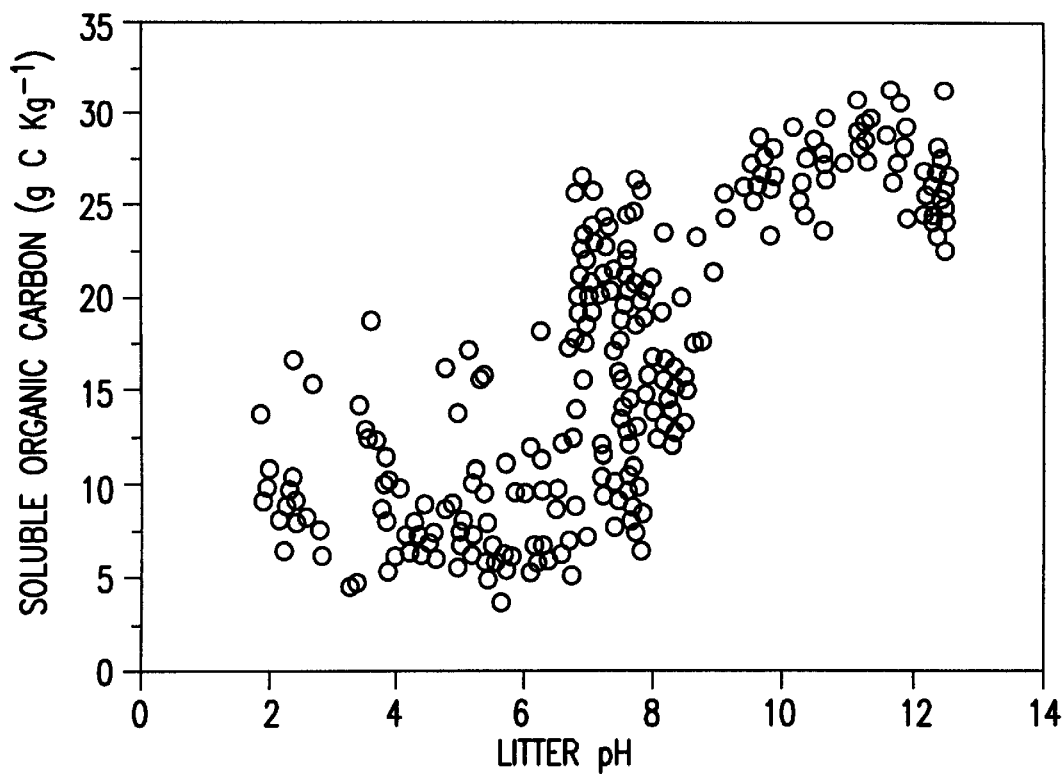
FIG. 10 illustrates the effect of poultry litter pH on soluble organic carbon.

Phosphorus accumulation onto calcite surfaces is characterized as a three step process: (1) chemisorption of phosphate onto the surface causing the formation of amorphous calcium phosphate nuclei; (2) a slow transformation of the nuclei into crystalline apatite; and (3) crystal growth of apatite. In our study, this process may have been inhibited by the high SOC levels in these treatments. High soluble carbon levels were measured in the extracts of samples which had relatively high pHs. This is shown in FIG. 10.

Our studies further reveealed that gypsum ($CaSO_4 2 H_2O$) decreased SRP from over 2000 mg phosphorus $kg^{-1}$ to approximately 700 mg phosphorus $kg^{-1}$ at the 100 g $kg^{-1}$ rate as shown in FIG. 9. It should be noted that the lowest rate of gypsum used in this study was high enough to exceed the solubility product of gypsum (2.4 g $L^{-1}$). This helps to explain why increasing rates of this compound did not influence phosphorus, which is that water soluble calcium levels will not be expected to increase after the solubility has been exceeded. If the reduction in SRP noted with the gypsum treatment was due to the formation of calcium phosphate mineral(s), phosphorus removal could be enhanced with this amendment if the pH were increased to 8 or higher. If adsorption of phosphorus by gypsum was the dominant mechanism of phosphorus removal with this amendment, then concentrations of phosphorus should have decreased with increasing rates of gypsum. However, this was not observed.

The addition of $CaF_2$ did not increase phosphorus removal in the calcium treatments, suggesting that fluorapatite formation did not occur. This could have been due to the presence of organic acids, Mg and $HCO_3$, both of which are known to inhibit apatite formation. Mineral equilibria studies have shown also that when calcium phosphates are forming, the solubility is intermediate between octacalcium phosphate ($Ca_4H(PO_4)_3$ 2.5 $H_2O$) and beta tricalcium phosphate ($\beta$-$Ca_3(PO_4)_2$).

(2) Aluminum and Iron Amendments

Figure 11:
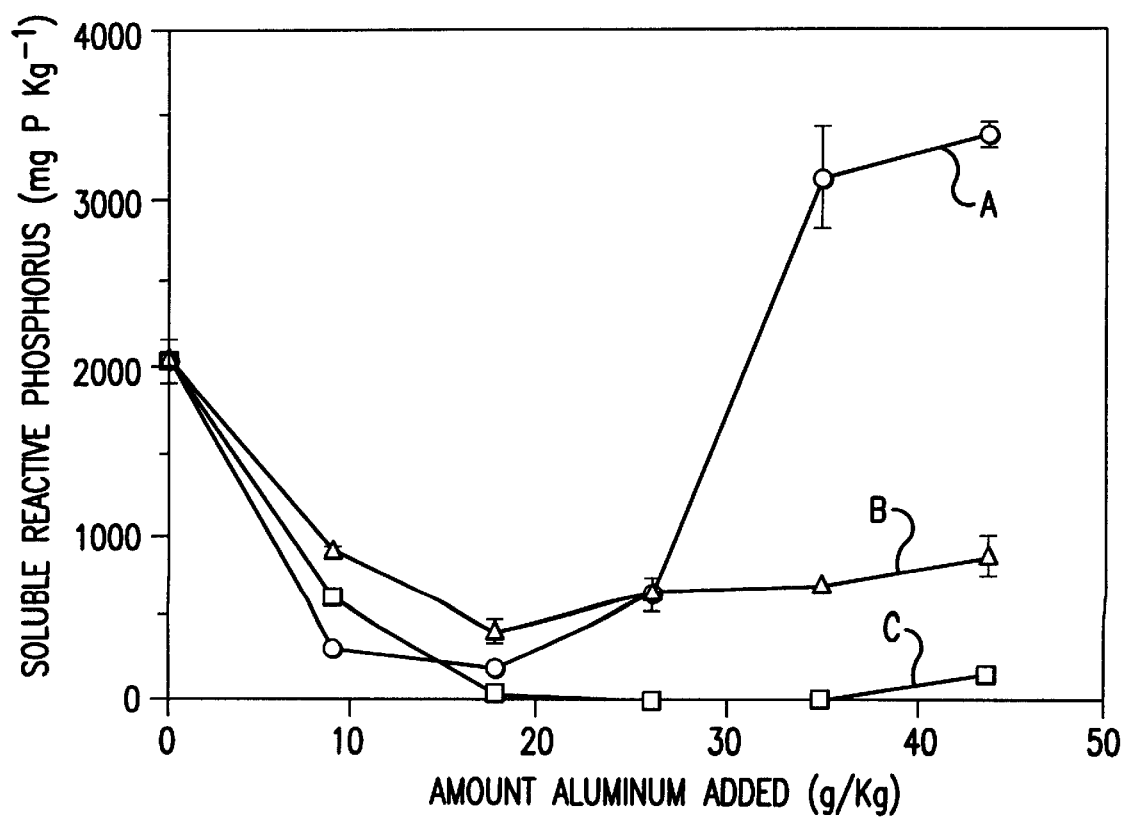
FIG. 11 illustrates the effect of aluminum amendments to poultry litter on water soluble reactive phosphorus. Plot A represents alum. Plot B represents sodium aluminate. Plot C represents alum plus calcite.

Alum additions greatly decreased water soluble phosphorus as illustrated in FIG. 11. Without $CaCO_3$ to buffer the pH, water soluble phosphorus increased at the highest alum rates. This was believed to be due to the acidity created by the alum, which may have caused: (1) dissolution of inorganic calcium phosphates; (2) acid hydrolysis of organic phosphorus; and/or (3) dissolution of $Al(OH)_3$, which would result in phosphorus release if adsorption had been the primary mechanism of removal. The pH of the alum treated litter dropped to 3.5 at the highest rate. This is shown in Table 3. Calcium phosphate minerals are highly soluble at this pH and could release enough phosphorus to achieve the phosphorus concentrations noted at the higher rates. Dicalcium phosphate is added to poultry feed to help insure proper bone development, since most of the phosphorus in soybean and corn is phytate phosphorus, which is unavailable to chickens since they lack the phytase enzyme.

As further illustrated in FIG. 11, when $CaCO_3$ was added with the alum to buffer the pH, virtually 100% of the soluble phosphorus was removed from solution. The optimum pH range for removal by Al has been shown to be from 5.5 to 8.0. Under acidic conditions (pH<6), $AlPO_4$ forms, while at pH 6 to 8, an $Al(OH)_3$ floc forms, which removes phosphorus from solution by sorption of inorganic phosphate and entrapment of organic particles containing phosphorus.

Other positive aspects anticipated with this invention include decreasing soluble organic carbon (SOC) levels in runoff water from litter-amended fields. As shown in FIG. 10, soluble organic carbon levels were relatively low under acidic conditions, whereas they tended to be high in the controls and in treatments which increased the pH of the litter. Decreases in SOC concentrations and associated reductions in biological oxygen demand of wastewaters are one of the primary functions of flocculents used in waste water treatment. Decreases in SOC runoff should also improve water quality by decreasing $O_2$ demand in lakes and rivers receiving runoff from pastures amended with poultry litter treated with acid forming products. Addition of metal flocculents also decreased the solubility of Cu and Zn, which occur in high concentrations in poultry litter. Minimum solubility of both of these metals occurred at approximately pH 6.

Sodium aluminate decreased SRP levels to around 600 mg phosphorus $kg^{-1}$ litter at the lowest rate. This is shown in FIG. 11. Increasing rates of sodium aluminate did not decrease water soluble phosphorus, which was probably due to elevated pH at the higher rates. Further, calcitic limestone, as an additive to the sodium aluminate treatment, did not decrease soluble phosphorus.

Figure 12:
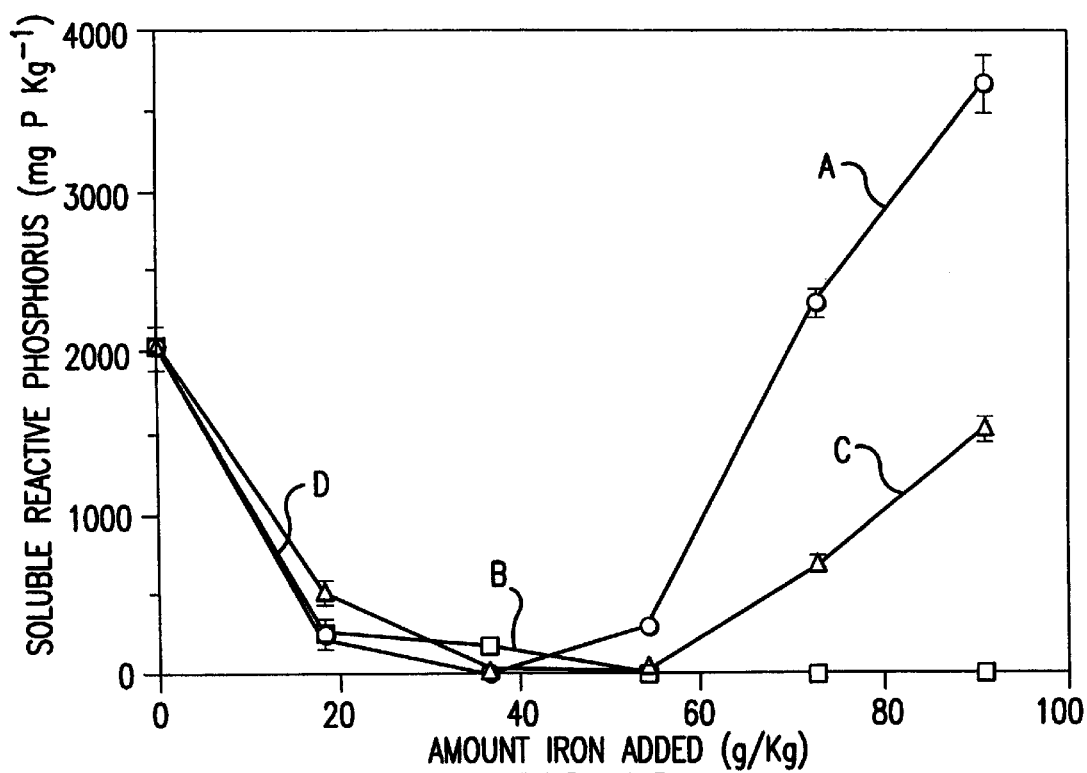
FIG. 12 illustrates the effect of iron amendments to poultry litter on water soluble reactive phosphorus. Plot A represents ferric chloride. Plot B represents ferrous chloride. Plot C represents ferric sulfate. Plot D represents ferrous sulfate.

FIG. 12 illustrates the effect of iron amendments to poultry litter on water soluble reactive phosphorus. Additions of ferric iron as $Fe_2(SO_4)_3 2 H_2O$ or $FeCl_3$ greatly decreased phosphorus solubility at the lower rates, but increased the solubility at the higher rates. Increases in SRP at the higher rates may have been due to: (1) dissolution of calcium phosphates; (2) acid hydrolysis of organic phosphorus; and/or (3) a decrease in adsorption of phosphorus by iron compounds due to dissolution of iron oxides and hydroxides at low pH. The pH of these two treatments approached 2 at the higher rates, which is shown in Table 3. These values are well below the optimum pH range (4.7 to 7.1) for phosphorus removal by iron reported previously in the literature. Therefore, removal with these compounds would have been enhanced if the pH of the litter had been maintained at a higher value.

The results from the study further indicate that pH adjustment is also necessary for Fe(III) systems which contain $SO_4$, such as the $Fe_2(SO_4)_3 2 H_2O$ treatment, because when extremely acid conditions occur, water soluble phosphorus levels increase dramatically.

As further illustrated in FIG. 12, ferrous sulfate ($FeSO_4$ 7 $H_2O$) additions greatly decreased the solubility of phosphorus in poultry litter. Water soluble phosphorus concentrations were not significantly different in the $FeSO_4$ treatment amended with $CaCO_3$, indicating that phosphorus removal with this compound is less pH dependent than for some of the other iron compounds. Additions of ferrous chloride greatly decreased phosphorus solubility. Additions of calcitic limestone in conjunction with ferrous chloride resulted in more efficient phosphorus removal at lower rates than ferrous chloride alone.

(C) Litter Management

Recently, there has been increasing emphasis on decreasing runoff of bioavailable phosphorus, rather than particulate phosphorus, since it is more available for use by algae that are responsible for eutrophication. Water soluble phosphorus is by far the most available form of phosphorus to algae and bacteria. Drastic reductions in soluble phosphorus levels running off agricultural lands receiving poultry litter should help improve the water quality of adjacent lakes and rivers.

It should be noted that alum and lime are relatively inexpensive and readily available. Calcium compounds, such as $CaO$ or $Ca(OH)_2$, cost approximately $55 per metric ton. Results from the present invention indicate that 50 kg of $Ca(OH)_2$ per metric ton of litter may be adequate to immobilize most of the litter phosphorus. Since there are 20 metric tons of litter produced per poultry house per growout (each house contains 15,000 to 20,000 birds), one ton of $Ca(OH)_2$ (slaked lime) is needed per house per growout. Assuming five growouts per year, the annual cost of slaked lime for one house would be $275. Gross incomes per house normally exceed $25,000 per year. Therefore, the cost of slaked lime needed for phosphorus immobilization would be around 1% of the gross income, which should be economically feasible. However, before a valid economic analysis of this process can be made, on-farm experiments need to be conducted to determine if treatment levels found in this study are adequate.

Although alum and ferrous sulfate are more expensive than $Ca(OH)_2$, the benefits of using these compounds should far exceed that of the calcium compounds. Lowering the pH of the litter will decrease $NH_3$ volatilization. High levels of $NH_3$ in poultry houses increase the incidence of ascites in poultry (water belly) and other respiratory related maladies, such as New Castle Disease and airsacculitus. Since the amount of $NH_3$ volatilization is a function of the ratio of $NH_3/NH_4$ in the litter, which is controlled by pH, reducing the pH of the litter to around 6.0 will cause nitrogen losses via this mechanism to cease. This should result in increased weight gains in the birds, as well as decreased incidence of respiratory problems.

Currently, the number one complaint received by federal and state regulatory agencies concerning poultry production concerns odors arising from land application of litter. Ammonia is one of the primary agents responsible for the odor. It is estimated that 37% of the nitrogen is lost from litter during the first 11 days of application. If these losses were combined with those that occur in the poultry houses, the total loss by volatilization would probably exceed 50% of the total nitrogen. Therefore, volatilization losses not only result in air pollution, but in losses of valuable fertilizer nitrogen. Decreasing $NH_3$ volatilization will result in higher nitrogen/phosphorus ratios in poultry litter. Currently, the nitrogen/phosphorus ratio in litter is often as low as 2, whereas this ratio in the feed is near 8. The difference is mainly due to nitrogen loss via volatilization. Since application rates of litter are based on the nitrogen requirement of the crop, less litter could be applied per acre if the nitrogen content were higher.

EXAMPLE 5

Reduction of Phosphorus In Runoff From Field-Applied Poultry Litter Using Chemical Amendments (A) Methods and Materials The use of poultry litter as a source of crop nutrients has been well established. The University of Arkansas Cooperation Extension Service recommends an annual maximum application rate of 11.2 Mg/ha, with no more than 5.6 Mg/ha in a single application. This recommendation is based on meeting the nitrogen requirements of forage, a common approach in animal waste application programs. Recommendations, however, based on forage nitrogen requirements do not consider other possible limiting factors in land application of poultry litter, such as phosphorus or heavy metal content. Field application of poultry litter at rates to meet forage nitrogen requirements normally results in an over-application of phosphorus. This study was conducted to determine the effects of two chemical amendments, alum and ferrous sulfate, on phosphorus concentrations and load in runoff and to evaluate the effects of amended litter on forage production.

The study was conducted on 1.5 m by 6.0 m (long axis oriented up- and down-slope) plots constructed at the Main Agricultural Experiment Station on a Captina silt loam (fine-silty, mixed, mesic Typic Fragiudult). Plots were graded to a uniform 5% slope and have rust-proofed metal borders (0.1 m below ground and 0.1 m above ground) to isolate runoff. An aluminum gutter attached to a 0.1-m horizontal approach plate was installed at the down-slope end of plots to facilitate collection of runoff. The soil-gutter interface was stabilized by means of a 0.1 m lip normal to the approach plate pushed vertically into the soil. Separation distance between plots are 0.75 m side to side and 3.0 m end to end. A stand of fescuegrass (*Festuca arundinacea* Schreb.) was established on the plots by seeding at approximately 500 kg/ha.

Soil samples were taken from the surface 15 cm of each plot, and available $PO_4$-P (Mehlich III) was determined. The experimental design was a modified randomized complete block design with 3 replications of 4 treatments consisting of a control (no litter), poultry litter alone, poultry litter plus alum, and poultry litter plus ferrous sulfate. Treatments were randomized among plots in each block such that mean soil test phosphorus levels were approximately equal between treatments as shown below in Table 4.

TABLE 4

Mean soil test P levels in plots of the various treatments.

| Treatment | Soil test P | |
|---|---|---|
| | Mean | S.D. |
| | (mg/kg) | |
| Litter + alum | 143 | 30 |
| Litter + ferrous sulfate | 143 | 19 |
| Litter alone | 144 | 16 |
| Control | 142 | 40 |

Litter was broadcast at the rate of 11.2 Mg/ha (dry weight basis). Chemical amendments were incorporated into litter prior to broadcasting at a 1:5 (w/w) ratio. Plots received 1.0 cm of precipitation from rainfall simulators 24 hours after litter was broadcast. Plots were covered during naturally-occurring rainstorms to prevent runoff.

Rainfall simulators (Edwards et al., *Arkansas Farm Research* 42(2):13–14, 1992) were used to provide 5 cm/hr precipitation events 2, 9, and 16 days after litter application. Runoff was collected during each event at 2.5, 7.5, 12.5, 17.5, 22.5, and 27.5 minutes after continuous runoff was observed. Time to runoff was recorded for each plot, and collection time and volume were recorded for each runoff sample. Total runoff volume and runoff rate were then calculated from these parameters.

A portion of each sample was filtered through a 0.45 $\mu$m membrane and acidified to pH 2 with concentrated HCl. Soluble reactive phosphorous concentrations were determined calorimetrically in the filtered, acidified samples. Phosphorus load from each plot was calculated from phosphorus concentration and runoff rate.

Plots were harvested 2 weeks and 4 weeks after the last precipitation event by mowing the entire plot to a 10 cm height and weighing all forage. Samples were retained from each prior plot for determination of moisture and nutrient content.

(B) Results

Figure 13A:
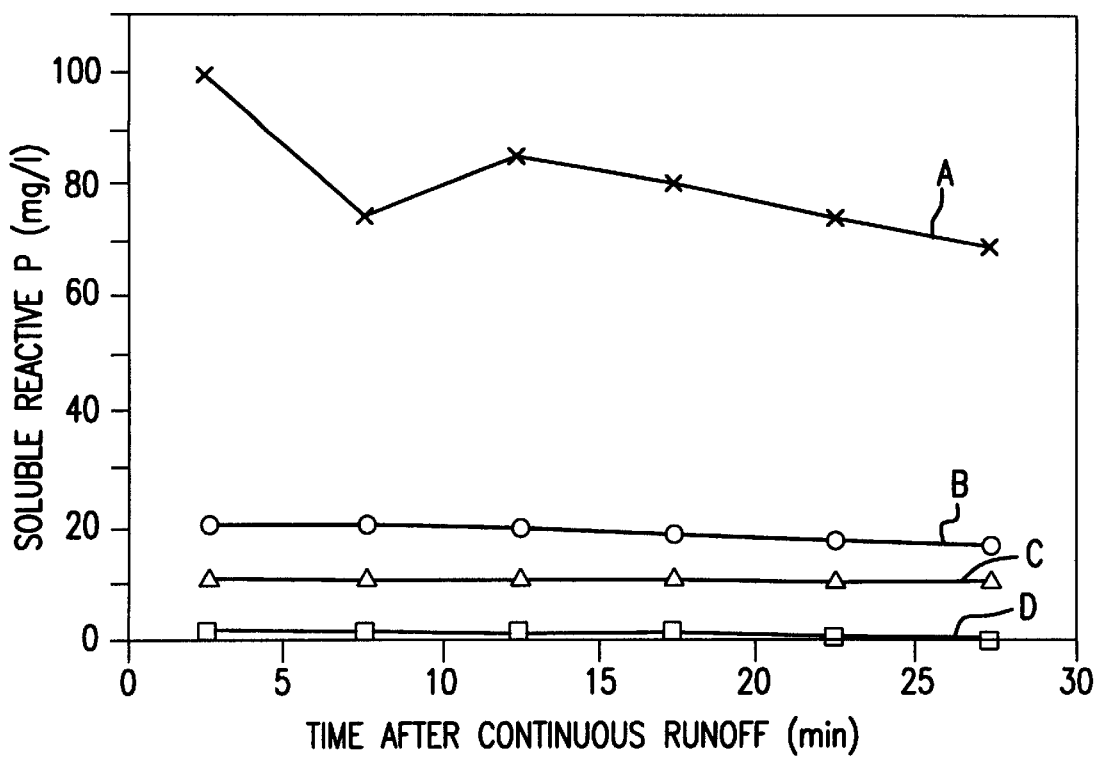
FIG. 13A illustrates the treatment effects on soluble reactive phosphorus concentrations in a first runoff event based on a simulated rainfall event. Plot A represents litter alone. Plot B represents litter plus ferrous sulfate. Plot C represents litter plus alum. Plot D represents the control.
Figure 13B:
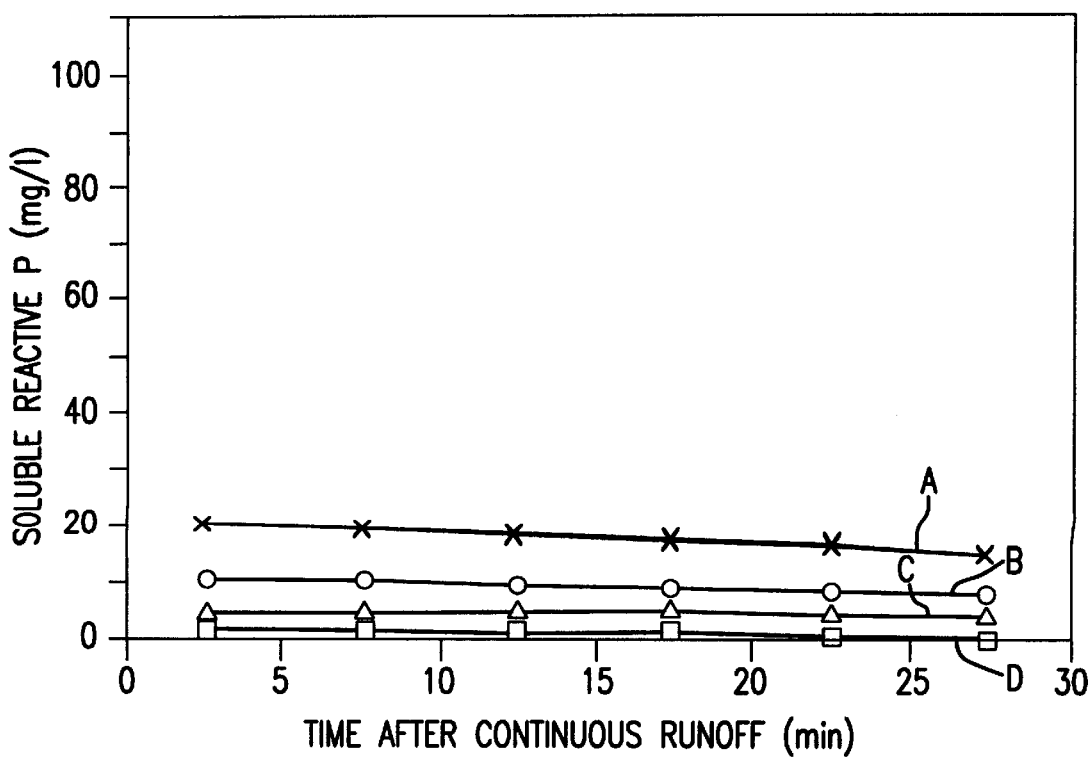
FIG. 13B illustrates treatment effects on soluble reactive phosphorus concentrations in a second runoff based on a simulated rainfall event. Plot A represents litter alone. Plot B represents litter plus ferrous sulfate. Plot C represents litter plus alum. Plot D represents the control.

Runoff phosphorus concentrations for the first and second runoff events are presented in FIGS. 13A and 13B, respectively. Amending poultry litter with alum resulted in an 87% reduction in phosphorus runoff concentration compared to litter alone for the first runoff event and a 63% reduction for the second runoff event. Poultry litter amended with ferrous sulfate also displayed a decrease in phosphorous runoff concentration (77% and 48% for the first and second runoff events, respectively). By the third runoff event, no differences were observed among the litter treatments.

Figure 14:
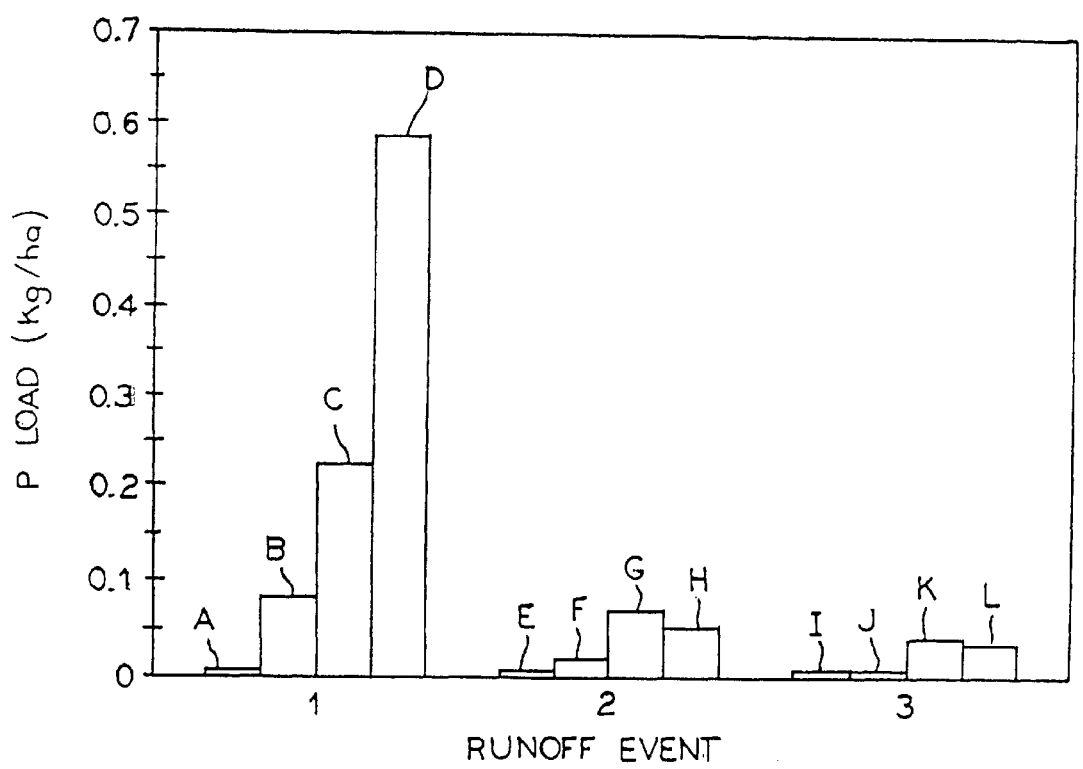
FIG. 14 illustrates the treatment effects on total phosphorus load from 3 runoff events. For runoff event 1, plot A represents the control. Plot B represents litter plus alum. Plot C represents litter plus ferrous sulfate. Plot D represents litter alone. For runoff event 2, plot E represents the control. Plot F represents litter plus alum. Plot G represents litter plus ferrous sulfate. Plot H represents litter alone. For runoff event 3, plot I represents the control. Plot J represents litter plus alum. Plot K represents litter plus ferrous sulfate. Plot L represents litter alone.

Alum and ferrous sulfate were successful in reducing total phosphorus load from the first runoff event, showing no difference from the control plots which had not received litter as shown in FIG. 14. No differences in total phosphorus load were observed between treatments after the first runoff event. Since most of the phosphorus load is in the first runoff event, the decreased phosphorus load resulting from chemically amending litter prior to application has important environmental implications.

Forage yield was increased by all litter treatments over the control for both first and second harvests as shown in Table 5 below. Total yield, however, showed a significant response to application of litter amended with alum over all other treatments.

TABLE 5

Mean forage yields from plots receiving chemically-amended poultry litter.

| Treatment | Mean Yield | | |
|---|---|---|---|
| | First Harvest | Second Harvest | Total |
| | (kg/ha) | | |
| Litter + alum | 801.7 | 1556.7 | 2358.3 |
| Litter + ferrous sulfate | 681.3 | 1292.3 | 1973.7 |
| Litter alone | 735.3 | 1111.7 | 1847.0 |
| Control | 278.7 | 454.3 | 733.0 |
| LSD (0.05) | 83.7 | 297.6 | 290.0 |

Alum-amended poultry litter decreased phosphorus concentration in runoff, decreased total phosphorus load, and increased forage yield. Chemically amending poultry litter with alum shows considerable promise as a management tool for limiting phosphorus inputs to surface water while increasing forage yields.

It should be understood that various changes and modifications to the presently preferred embodiments described herein will be apparent to those skilled in the art. Such changes and modifications can be made without departing from the spirit and scope of the present invention, and without diminishing its attendant advantages. It is therefore intended that such changes and modifications be covered by the appended claims.

I claim:

1. A method for inhibiting ammonia volatilization in poultry litter, comprising the steps of: admixing in situ alum to a poultry litter composition sample comprising poultry manure, bedding material, spilled food and feathers in an amount sufficient to maintain a pH of the resulting alum/poultry litter composition sample at less than 8.0.

2. A method as defined in claim 1, wherein said alum is admixed with the poultry litter composition in an amount of from about 5% to about 25% by weight based on dry weight of said poultry litter composition.

3. A method for making nitrogen enhanced fertilizer based on poultry litter comprising the steps of applying in situ a nitrogen content improving amount of alum to a poultry litter composition comprising poultry litter, bedding material, spilled food and feathers, to be used for fertilizer and thereafter admixing the alum and poultry litter composition.

4. A method as defined in claim 3, and further comprising the step of providing a sample of the alum and poultry litter composition wherein the amount of alum added is sufficient to maintain a pH value for the sample of the alum and poultry litter composition mixture after applying and mixing at less than 8.0.

5. A method for inhibiting ammonia volatilization in poultry litter, comprising the steps of:

(a) providing an enclosure for raising a flock of poultry;

(b) adding fresh bedding material to the enclosure;

(c) raising a flock of poultry in the enclosure through growout;

(d) removing the flock after growout;

(e) applying in situ alum to a poultry litter sample comprising poultry manure, bedding material, spilled food and feathers in said enclosure in an amount sufficient to maintain a pH of the resulting alum/poultry litter sample at less than about 8.0; and (f) admixing the alum in the sample.

6. A method as defined in claim 5, wherein steps (c) through (e) are repeated in sequence one or more times.

7. A method as defined in claim 5, wherein the alum is applied at the top of the poultry litter and then mechanically admixed into the poultry litter.

8. A method of inhibiting buildup of atmospheric ammonia in a commercial poultry rearing facility which comprises applying in situ and admixing alum to poultry litter in an amount sufficient to maintain the litter pH at values sufficiently low to inhibit the buildup of atmospheric ammonia in the poultry rearing facility.

9. A method as defined in claim 8, wherein the alum is applied at the top of the litter and then mechanically admixed into the litter.

* * * * *